United States Patent
Yamaguchi et al.

(10) Patent No.: US 8,626,273 B2
(45) Date of Patent: Jan. 7, 2014

(54) ELECTRONIC ENDOSCOPE SYSTEM HAVING PROCESSOR DEVICE, AND METHOD FOR PROCESSING ENDOSCOPIC IMAGE

(75) Inventors: Hiroshi Yamaguchi, Kanagawa (JP); Takayuki Iida, Kanagawa (JP); Hiroaki Yasuda, Kanagawa (JP); Takashi Murooka, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 50 days.

(21) Appl. No.: 13/281,246

(22) Filed: Oct. 25, 2011

(65) Prior Publication Data

US 2012/0101348 A1   Apr. 26, 2012

(30) Foreign Application Priority Data

Oct. 26, 2010 (JP) .................................. 2010-239857

(51) Int. Cl.
*A61B 6/00* (2006.01)
(52) U.S. Cl.
USPC ........................... 600/478; 600/476; 600/473
(58) Field of Classification Search
USPC ................................................ 600/473–480
See application file for complete search history.

(56) References Cited

U.S. PATENT DOCUMENTS

| | | | |
|---|---|---|---|
| 5,523,786 A | 6/1996 | Parulski | |
| 5,827,190 A * | 10/1998 | Palcic et al. | 600/476 |
| 7,573,499 B2 * | 8/2009 | Doguchi et al. | 348/65 |
| 2003/0189663 A1 | 10/2003 | Dolt et al. | |
| 2004/0263645 A1 * | 12/2004 | Okada et al. | 348/231.99 |
| 2008/0306337 A1 | 12/2008 | Livingston et al. | |
| 2009/0036743 A1 | 2/2009 | Yabe et al. | |
| 2009/0192348 A1 * | 7/2009 | Nishino | 600/103 |
| 2011/0184236 A1 * | 7/2011 | Yoshino | 600/109 |
| 2012/0101348 A1 * | 4/2012 | Yamaguchi et al. | 600/317 |

FOREIGN PATENT DOCUMENTS

| | | |
|---|---|---|
| EP | 2 082 680 A1 | 7/2009 |
| JP | 7-240931 A | 9/1995 |
| JP | 2001-161696 A | 6/2001 |
| JP | 2001-170009 A | 6/2001 |
| JP | 2003-88498 A | 3/2003 |
| WO | WO 2011/131277 A1 | 10/2011 |

OTHER PUBLICATIONS

European Search Report dated Jan. 6, 2012.
Notification of Reason(s) for Refusal dated Feb. 14, 2013, with English translation.

\* cited by examiner

*Primary Examiner* — Sanjay Cattungal
(74) *Attorney, Agent, or Firm* — McGinn Intellectual Property Law Group, PLLC

(57) ABSTRACT

White light and excitation light are applied to an internal body part. An electronic endoscope captures a normal image of the internal body part irradiated with the white light, and a special image of autofluorescence emitted from living body tissue of the internal body part irradiated with the excitation light. An object distance detector detects an object distance between a CCD and an inspection area of the internal body part based on the normal image. A binning processing section applies a binning process to the special image. There are two types of binning processes, i.e. an intensity adjustment process and a resolution adjustment process. In the intensity adjustment process, the binning number is increased with increase in the object distance. In the resolution adjustment process, the binning number is decreased with increase in the object distance. Which process to perform is determined by operation on a processing type selector.

14 Claims, 17 Drawing Sheets

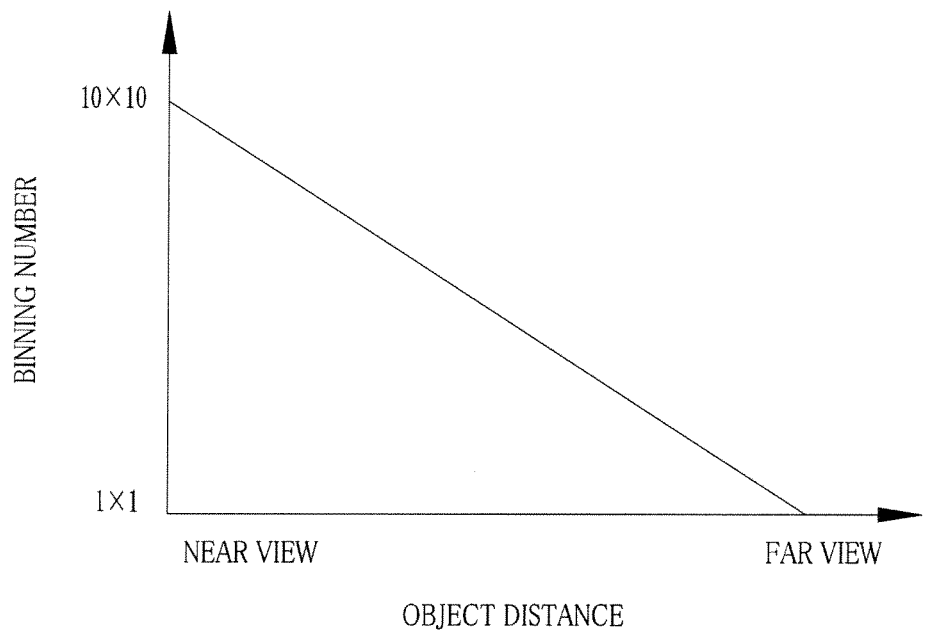

ELECTRONIC ENDOSCOPE SYSTEM HAVING PROCESSOR DEVICE, AND METHOD FOR PROCESSING ENDOSCOPIC IMAGE

BACKGROUND OF THE INVENTION

1. Field of the Invention

The present invention relates to an electronic endoscope system having a special imaging function such as autofluorescence imaging (AFI) and narrow band imaging (NBI).

2. Description Related to the Prior Art

In a medical field, diagnosis and treatment using an electronic endoscope system are widely carried out in recent years. In the electronic endoscope system, while white light (normal light), which ranges from a blue wavelength band to a red wavelength band, is applied to the inside of a patient's body cavity, an image sensor such as a CCD captures an image of the light reflected from an internal body part. The captured image is displayed on a monitor. The electronic endoscope system can image the inside of the human body cavity in real time, and facilitates the accurate diagnosis and the effective treatment.

The image (normal image) captured under the normal light shows an overview of the internal body part, but cannot clearly show a capillary blood vessel, an underlying blood vessel, a pit pattern, and irregularities in surface tissue such as a depression or a lump. Since a pathologic lesion is sometimes hidden in such a portion or tissue, it is desired that the capillary blood vessel or the irregularities can be clearly seen in an endoscopic image.

As a method for imaging a tumor lesion including a cancer, for example, autofluorescence imaging (AFI) is known as described in US Application Publication No. 2009/0036743 (corresponding to Japanese Patent Laid-Open Publication No. 2009-34224). In the AFI, special light having a specific wavelength is applied as excitation light to the internal body part, and the image sensor captures an image of autofluorescence that is emitted from an endogenous fluorescent substance of living body tissue in response to the excitation light. According to the AFI, the intensity of the autofluorescence emitted from tumor tissue is weaker than that from normal tissue. Through the use of this property, the tumor lesion is colored differently from a normal portion in a special image. Thus, the tumor lesion is clearly distinguished in the special image, though it is hard to see in the normal image.

Narrow band imaging (NBI) is also known as a method for clearly imaging a superficial blood vessel, which is positioned in the shallow depth of the living body tissue, by application of special light having wavelengths in a specific narrow band, as described in Japanese Patent Laid-Open Publication No. 2001-170009. In the NBI, the superficial blood vessel is distinguished by taking advantage of a light absorbing property of the blood vessel that occurs upon application of the special light and a light scattering property of the living body tissue around the blood vessel. The special image facilitates finding out a lesion that is hard to find out in the normal image.

In a special imaging function such as the AFI and NBI, there is a need to obtain an optimal endoscopic image in accordance with various purposes of the image diagnosis. For example, in the case of trying to find out the lesion in the bright endoscopic image on a whole, the image requires enough intensity even in a far view in which a distal end portion of an electronic endoscope is away from the body part to be imaged. In the case of trying to find out the lesion from a minute portion of the image such as a clot in the blood vessel, the image requires resolution high enough to clearly discern the minute portion even in the far view. However, neither the US Patent Application Publication No. 2009/0036743 nor the Japanese Patent Laid-Open Publication No. 2001-170009 discloses or even suggests an electronic endoscope system that can obtain an optimal endoscopic image in accordance with various purposes.

SUMMARY OF THE INVENTION

An object of the present invention is to provide an electronic endoscope system that can obtain an optimal image in accordance with various purposes during performing a special imaging function including autofluorescence imaging (AFI) or narrow band imaging (NBI).

An electronic endoscope system according to the present invention includes a light source device, an electronic endoscope, an object distance detector, a binning processing section, and a binning processing control section. The light source device applies to an internal body part illumination light including special light in a specific wavelength band. The electronic endoscope captures an endoscopic image of the internal body part irradiated with the illumination light by using an image sensor. The endoscopic image includes a special image captured under the special light. The object distance detector detects from the endoscopic image an object distance being a distance between the image sensor and an inspection area of the internal body part. The binning processing section applies a binning process to the special image. The binning processing control section determines a binning number used in the binning process in accordance with the object distance.

The special light may be excitation light for exciting autofluorescence from living body tissue of the internal body part. The special image may be an autofluorescence image that captures autofluorescence emitted from the internal body part irradiated with the excitation light.

The binning processing control section preferably increases the binning number with increase in the object distance, and decreases the binning number with decrease in the object distance, in order to adjust intensity of the autofluorescence image. Furthermore, the binning processing control section preferably decreases the binning number with increase in the object distance, and increases the binning number with decrease in the object distance, in order to adjust resolution of the autofluorescence image.

The special light may be NBI light for distinguishing a specific portion including a superficial blood vessel, and the special image may be an NBI image of the internal body part irradiated with the NBI light. In another case, the special light may be narrow band light used for obtaining blood vessel information including a depth of a blood vessel and blood oxygen saturation. The narrow band light includes two types of light having first and second wavelengths. Absorbance of reduced hemoglobin differs from that of oxygenated hemoglobin at each of the first and second wavelengths, and an amount of difference in the absorbance between the reduced hemoglobin and the oxygenated hemoglobin at the first wavelength differs from that at the second wavelength. The special image may be a blood vessel information image of the internal body part irradiated with the narrow band light.

The binning processing control section may increase the binning number with increase in the object distance between a near view having a short object distance and a far view having a long object distance. Also, the binning processing control section may set the binning number larger in a tight close-up state than that in a close-up state. The image sensor is extremely near the inspection area of the internal body part in the tight close-up state, and the image sensor is slightly away from the inspection area in the close-up state as compared to the tight close-up state.

The electronic endoscope system may further include an imaging mode switching section for switching the electronic endoscope system to a special imaging mode. The special imaging mode includes an AFI mode for capturing an autofluorescence image that captures autofluorescence emitted from living body tissue in response to the excitation light applied from the light source device to the internal body part, an NBI mode for capturing an NBI image in which a specific portion including a superficial blood vessel is distinguished by applying the NBI light from the light source device to the internal body part, and a blood vessel information obtaining mode for capturing an image of blood vessel information including a depth of a blood vessel and blood oxygen saturation by applying the narrow band light from the light source device to the internal body part. The binning processing control section preferably determines the binning number in accordance with a type of the special imaging mode and the object distance.

The binning processing section may perform a software binning process in which the special image is constituted of plural pixel groups each of which includes plural adjoining pixels, and intensity of each pixel group corresponds with a sum of intensity of the pixels contained in the pixel group. In another case, the binning processing section may perform a hardware binning process in which the image sensor is constituted of plural pixel groups each which includes plural adjoining pixels, and the image sensor is controlled so as to output a single imaging signal on a pixel group basis. In either case, the binning number is a number of the pixels contained in each pixel group.

The illumination light may include normal light being white light ranging from a blue wavelength band to a red wavelength band. The endoscopic image may include a normal image of the internal body part irradiated with the normal light. The object distance detector may obtain the object distance from the normal image. Furthermore, the object distance detector may detect an exposure amount from the normal image, and calculates the object distance in accordance with the detected exposure amount.

The electronic endoscope system may further include a motion detector for detecting motion of the inspection area of the internal body part from a plurality of the endoscopic images, a frame addition section for applying a frame addition process to a plurality of the special images to produce a single high-quality special image, and a frame addition control section for determining a number of frames to be added in the frame addition process in accordance with the motion of the inspection area detected by the motion detector.

According to the present invention, when the binning process is applied to the special image such as the autofluorescence image, the binning number is determined in accordance with the object distance, which has an influence on the intensity and resolution of the special image. Therefore, it is possible to produce an optimal image that is adequate for its purpose.

BRIEF DESCRIPTION OF THE DRAWINGS

For more complete understanding of the present invention, and the advantage thereof, reference is now made to the following descriptions taken in conjunction with the accompanying drawings, in which:

FIG. 14 is a graph showing the relation between the binning number and the object distance in a resolution adjustment process;

FIG. 15 is an explanatory view of a lookup table (LUT) for storing the object distance and the binning number in relation to each other;

DESCRIPTION OF THE PREFERRED EMBODIMENTS

First Embodiment

Figure 1:
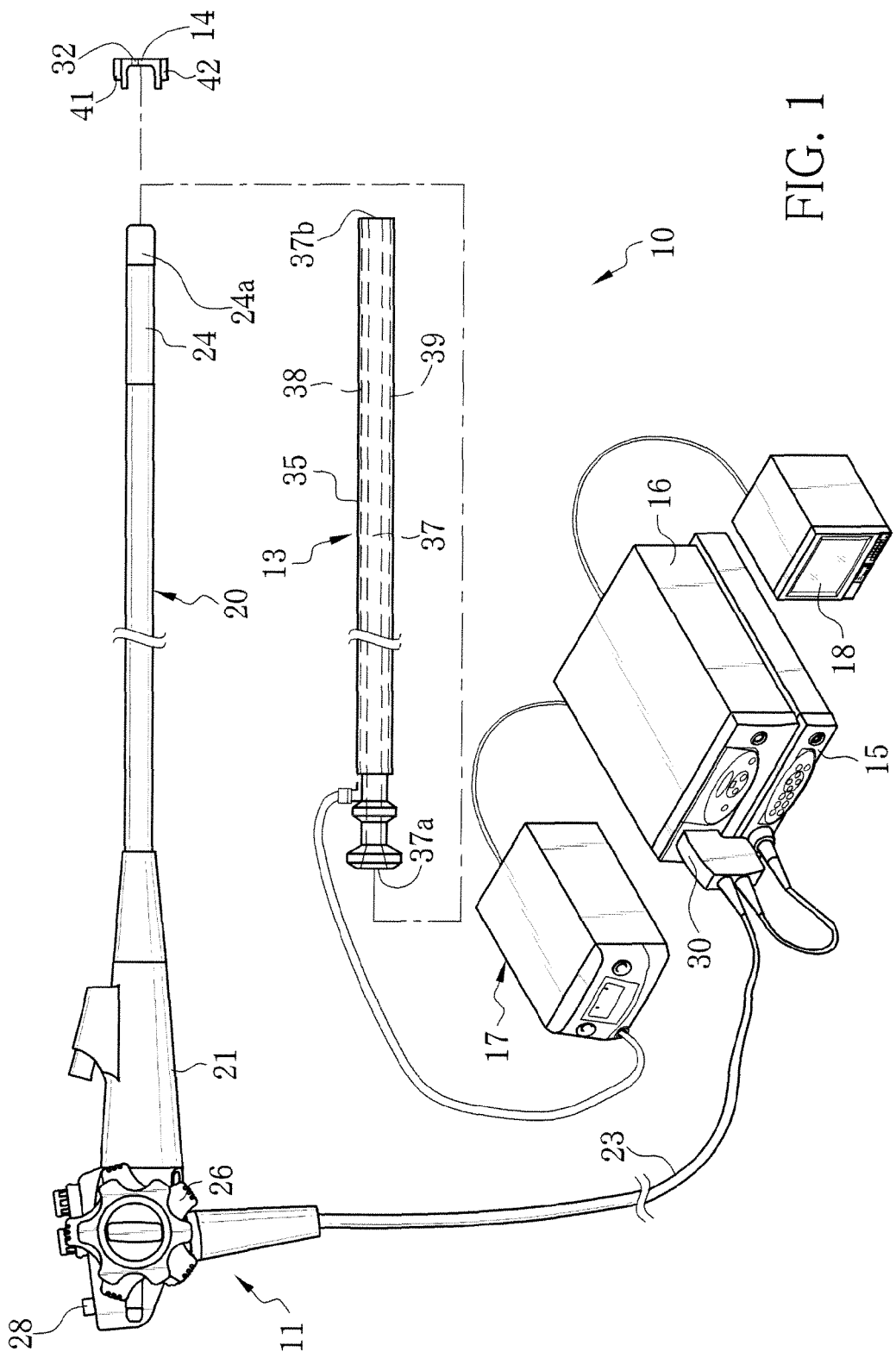
FIG. 1 is a schematic view of an electronic endoscope system according to a first embodiment.

An electronic endoscope system 10 of a first embodiment, as shown in FIG. 1, has an autofluorescence imaging (AFI) function for imaging autofluorescence emitted from living body tissue inside a patient's body cavity. The electronic endoscope system 10 is provided with an electronic endoscope 11, an over-tube 13, a hood 14, a processor device 15, a normal light source device 16, a special light source device 17, and a monitor 18. The electronic endoscope 11 captures an image inside the patient's body cavity with an image sensor such as a CCD. Into the over-tube 13, an insert section 20 of the electronic endoscope 11 is inserted. The hood 14 is attached to a distal end portion 24a of the insert section 20. The processor device 15 produces an endoscopic image of the internal body part based on a signal obtained by the CCD. The normal light source device 16 supplies white light (normal light) to irradiate the internal body part therewith. The special light source device 17 supplies excitation light (special light) that excites the autofluorescence from the living body tissue. The monitor 18 displays the endoscopic image.

The electronic endoscope 11 includes the flexible insert section 20 to be introduced into the patient's body cavity, an operation section 21 provided on a proximal end of the insert section 20, and a universal cord 23 for connecting the operation section 21 to both the processor device 15 and the normal light source device 16. At a distal end of the insert section 20, there is formed a bending portion 24, which is composed of a plurality of joint pieces coupled to one another. The bending portion 24 flexibly bends up or down or from side to side in response to operation of an angle knob 26 provided on the operation section 21.

Figure 4:
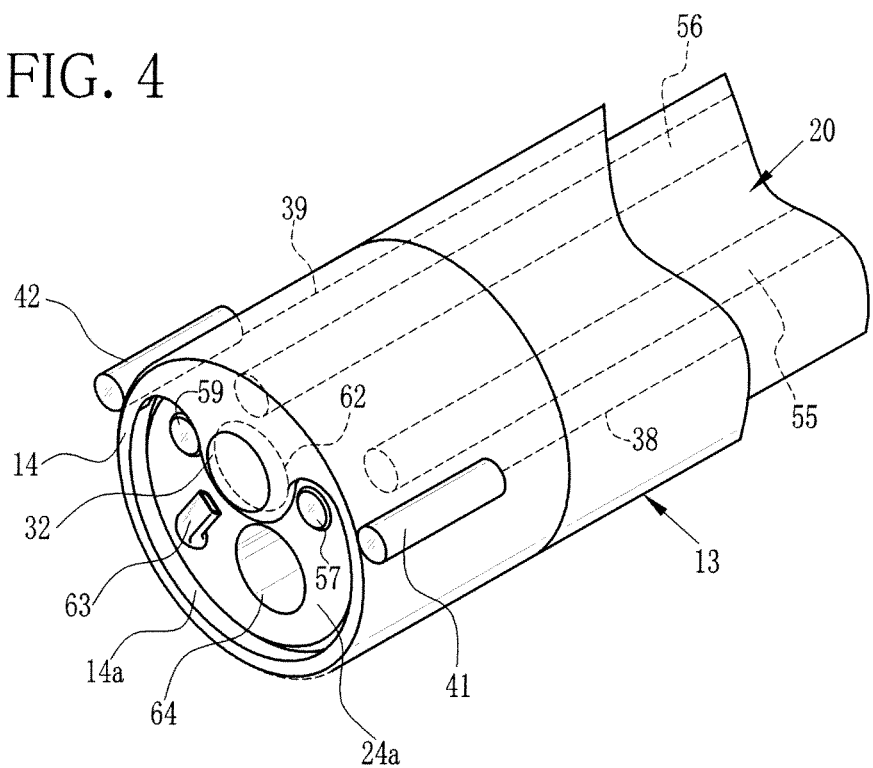
FIG. 4 is a perspective view of a distal end portion of an electronic endoscope according to the first embodiment to which an over-tube and a hood are attached.

The distal end portion 24a is provided at an end of the bending portion 24. The distal end portion 24a contains an optical system for endoscopy and the like. The distal end portion 24a is aimed at a desired direction inside the body cavity by flexibly bending the bending portion 24. As shown in FIG. 4, the distal end portion 24a is provided with first and second lighting windows 57 and 59 for projecting the white light or the excitation light, an imaging window 62 for receiving the reflected white light or the autofluorescence from the internal body part, an airing/watering nozzle 63 for spraying water or ejecting air to the imaging window 62, and a medical instrument outlet 64 from which a medical instrument led through a channel of the insert section 20 protrudes.

An imaging mode switching button 28 is provided on the operation section 21 to switch the electronic endoscope system 10 between a normal imaging mode for imaging the internal body part with the white light and a special imaging mode for imaging the autofluorescence emitted from the living body tissue upon application of the excitation light. Mode switching information is sent to a system controller 113 (see FIG. 2) of the processor device 15.

In the normal imaging mode, a normal image that is an image of the white light reflected from the internal body part is displayed on the monitor 18. In the special imaging mode, on the other hand, a special image that is an image of the autofluorescence or a composite image of the normal image and the special image is displayed on the monitor 18.

A connector 30 is attached at one end of the universal cord 23 on the side of the processor device 15 and the normal light source device 16. The connector 30 is a complex connector that has a communication connector to be coupled to the processor device 15 and a lighting connector to be coupled to the normal light source device 16. The electronic endoscope 11 is detachably connected to the processor device 15 and the normal light source device 16 via the connector 30.

Figure 2:
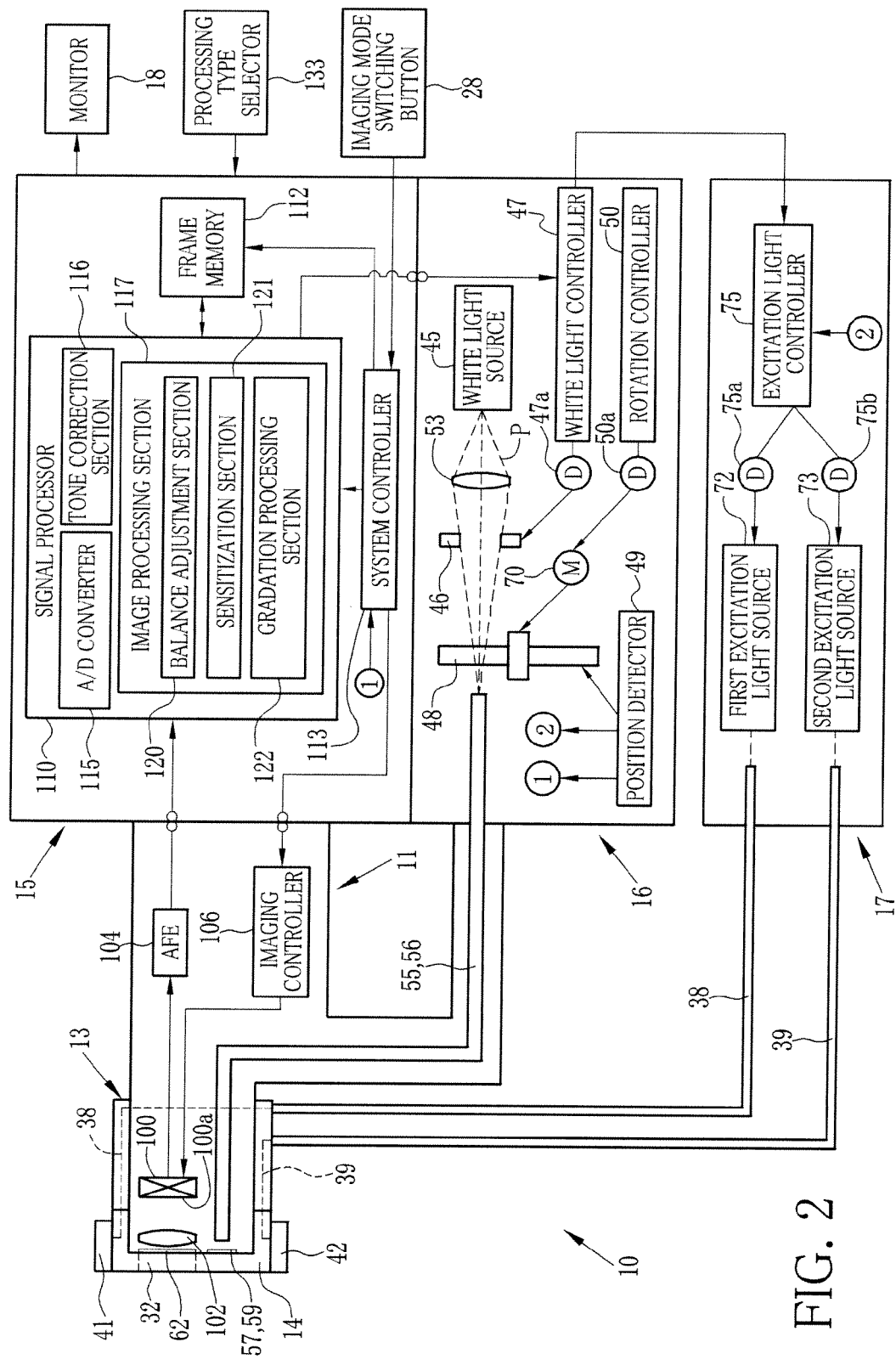
FIG. 2 is a block diagram of the electronic endoscope system according to the first embodiment.

As shown in FIGS. 1, 2, and 4, the hood 14 attached to the distal end portion 24a of the electronic endoscope 11 is provided with an excitation light cut filter 32. The excitation light cut filter 32 covers the imaging window 62 provided in the distal end portion 24a, in order to cut off part or all of light in a wavelength band of the excitation light out of light entering into the imaging window 62. The excitation light cut filter 32 cuts off the excitation light with high energy in front of the imaging window 62, and prevents the excitation light from entering into a CCD 100 disposed in the depth of the imaging window 62. This is effective at preventing the occurrence of halation by which electric charges become saturated at pixels of the CCD 100 and an image is bleached out.

The over-tube 13 includes a tube body 35, an insertion channel 37 provided inside the tube body 35, and first and second optical fibers 38 and 39. The insert section 20 of the electronic endoscope 11 is inserted into the insertion channel 37. The first and second optical fibers 38 and 39 are disposed on the periphery of the insertion channel 37 to lead the excitation light from the special light source device 17 therethrough.

The insertion channel 37 has a proximal opening 37a being an entrance of the insert section 20 of the electronic endoscope 11, and a distal opening 37b being an outlet of the insert section 20. When the insert section 20 is introduced into the insertion channel 37, the distal end portion 24a of the electronic endoscope 11 with the hood 14 attached protrudes from the distal opening 37b. The insert section 20 of the electronic endoscope 11 is introduced into the patient's body cavity in a state of being inserted in the over-tube 13. On the periphery of the hood 14, first and second light projection units 41 and 42 are adhered to project the excitation light from the first and second optical fibers 38 and 39 to the internal body part, respectively. Note that, the first optical fiber 38 and the first light projection unit 41 are optically coupled by a connector or the like. The second optical fiber 39 and the second light projection unit 42 are optically coupled by a connector or the like.

Figure 3:
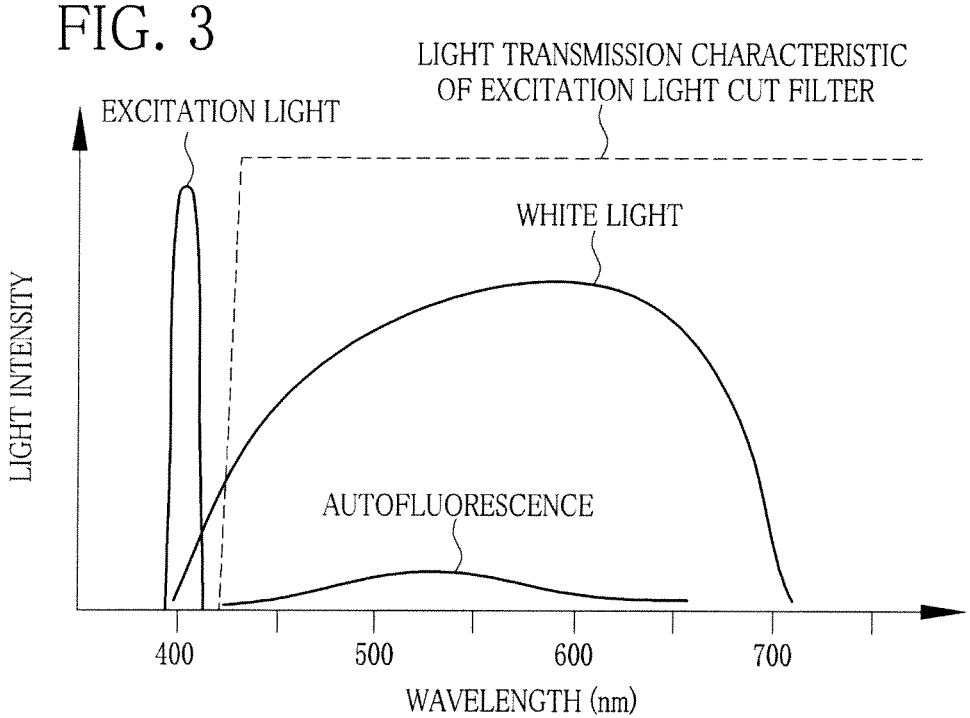
FIG. 3 is a graph showing spectrums of excitation light, autofluorescence, and white light, and a light transmission characteristic of an excitation light cut filter.

As shown in FIG. 2, the normal light source device 16 is constituted of a white light source 45, an aperture controller 46, a white light controller 47, a rotary shutter 48, a position detector 49, and a rotation controller 50. While the normal light source device 16 is turned on, the white light source 45 is invariably turned on and emits the white light. The white light is broad band light ranging from the blue wavelength band to the red wavelength band, and, for example, is in a wavelength band of 400 nm to 700 nm as shown in FIG. 3. As the white light source 45, a xenon lamp, a halogen lamp, an LED (light-emitting diode), a fluorescent lamp, or an LD (laser diode) is available by way of example. The white light emitted from the white light source 45 is condensed by a lens 53. After that, the condensed white light is incident upon first and second light guides 55 and 56 through the aperture controller 46.

The first and second light guides 55 and 56 are composed of optical fibers with a large diameter, or the like. A light incident end of each of the first and second light guides 55 and 56 is connected to the normal light source device 16. As shown in FIG. 4, a light exit end of the first light guide 55 is faced to the first lighting window 57 of the distal end portion 24a of the electronic endoscope 11. A light exit end of the second light guide 56 is faced to the second lighting window 59 of the distal end portion 24a. The white light is applied to the internal body part through the first or second lighting window 57 or 59.

Figure 5:
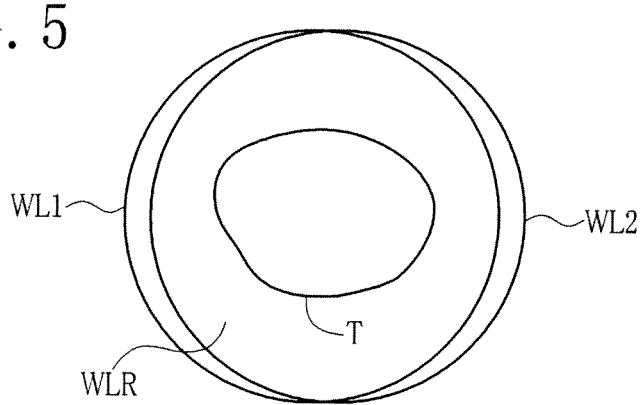
FIG. 5 is an explanatory view of irradiation areas of the white light.

The first and second lighting windows 57 and 59 are symmetric with respect to the excitation light cut filter 32 (or the imaging window 62) provided in the hood 14. As shown in FIG. 5, an irradiation area WL1 of the white light projected from the first lighting window 57 and an irradiation area WL2 of the white light projected from the second lighting window 59 overlap each other at a white light overlapping area WLR. The distal end portion 24a is aimed at a target area T such that the target area T is within the white light overlapping area WLR. Thus, the target area T is irradiated with the white light enough and uniformly.

The hood 14 covers only the imaging window 62 of the distal end portion 24a, and exposes the remaining portion of the distal end portion 24a to the outside in the body cavity. Thus, the hood 14 does not hinder the application of the white light from the first and second lighting windows 57 and 59. The air or water is sprayed from the airing/watering nozzle 63 to the excitation light cut filter 32 of the hood 14. The medical instrument protrudes from the medical instrument outlet 64 inside the body cavity.

As shown in FIG. 2, the aperture controller 46 disposed between the lens 53 and the rotary shutter 48 adjusts the amount of the white light emitted from the white light source 45. The aperture controller 46 is composed of, for example, plural blades for varying the size of an aperture, a motor for moving the blades, and the like. A set value of the aperture controller 46, that is, the amount of the white light to be passed through the aperture is controlled by the white light controller 47 via a driver 47a. The white light controller 47 controls the set value (the white light amount) based on the endoscopic image, which is obtained after signal processing by the processor device 15.

Figure 6A:
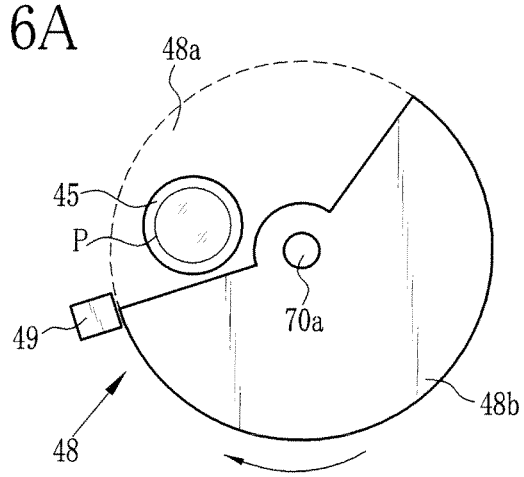
FIG. 6A is an explanatory view showing a state of a rotary shutter in a first period.
Figure 6B:
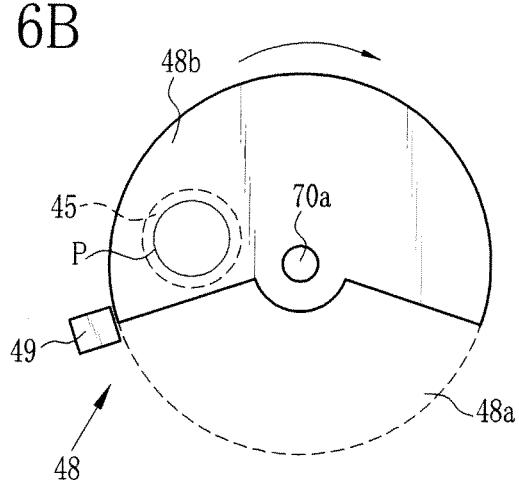
FIG. 6B is an explanatory view showing a state of the rotary shutter in a second period.

Referring to FIGS. 6A and 6B, the disc-shaped rotary shutter 48 has a sectorial cutout. The cutout of the rotary shutter 48 composes a light transmitting portion 48a for transmitting the white light. The remaining portion of the rotary shutter 48 composes a light shielding portion 48b for cutting out the white light. The rotary shutter 48 is coupled to a rotation axis 70a of the motor 70 disposed in parallel with an optical axis of the white light source 45. Since the rotary shutter 48 rotates by a drive of the motor 70, the light transmitting portion 48a and the light shielding portion 48b are alternately situated in an optical path P of the white light.

The position detector 49, composed of a photosensor or the like, detects which of the light transmitting portion 48a and the light shielding portion 48b is situated in the optical path P. Note that, in the FIGS. 2, 6A, and 6B, the position detector 49 is disposed in the vicinity of the rotary shutter 48 in such a position as to face a side edge of the rotary shutter 48, but may be disposed in another position. For example, the position detector 49 may be disposed so as to face a surface of the rotary shutter 48.

As shown in FIG. 6A, when the light transmitting portion 48a is situated in the optical path P, the white light is incident upon the first and second light guides 55 and 56. Thus, the internal body part is irradiated with the white light. This period is referred to as a first period. On the other hand, as shown in FIG. 6B, when the light shielding portion 48b is situated in the optical path P, the white light is not incident upon the first and second light guides 55 and 56. Thus, the internal body part is shielded from the white light. This period is referred to as a second period. The position detector 49 appropriately sends information about the first and second periods to an excitation light controller 75 of the special light source device 17 and the system controller 113 of the processor device 15.

The durations of the first and second periods depend on the selected imaging mode. The durations of the first and second periods in the special imaging mode are twice as long as those in the normal imaging mode. In other words, the rotation controller 50 shown in FIG. 2 controls the rotary shutter 48 in the special imaging mode at a rotation speed half of that in the normal imaging mode. The rotation controller 50 controls the rotation speed of the rotary shutter 48 via a driver 50a connected to the motor 70.

As shown in FIG. 2, the special light source device 17 includes first and second excitation light sources 72 and 73 and an excitation light controller 75. Each of the first and second excitation light sources 72 and 73 is composed of a light emitting diode or the like, and emits the excitation light having wavelengths of 405±10 nm, as shown in FIG. 3. By irradiating the internal body part with the excitation light in such a wavelength band, the autofluorescence having wavelengths of 420 nm to 650 nm is emitted from an endogenous fluorescent substance in the living body tissue.

In the special imaging mode, the excitation light is invariably emitted from the first and second excitation light sources 72 and 73. Thus, the living body tissue invariably emits the autofluorescence. As shown in FIG. 3, according to a light transmission characteristic of the excitation light cut filter 32, transmittance of short wavelength light having a wavelength of 415 nm or less is approximately zero. Accordingly, the excitation light reflected back to the distal end portion 24a of the electronic endoscope 11 is cut by the excitation light cut filter 32. The amount of the autofluorescence is much smaller than that of the white light. For these reasons, the excitation light and the autofluorescence hardly exerts an influence upon the normal image, even if the normal image is obtained in the presence of the excitation light and the autofluorescence in addition to the white light inside the patient's body cavity.

The excitation light controller 75 controls the light emission amount of the first and second excitation light sources 72 and 73 via drivers 75a and 75b, respectively. The excitation light controller 75 is connected to the white light controller 74, and controls the emission amount of the excitation light in accordance with the control of the emission amount of the white light by the white light controller 47. The emission amount of the excitation light is in correlation with the emission amount of the white light. The emission amount of the excitation light is changed such that the ratio between the emission amount of the excitation light and the emission amount of the white light is kept at 1/10, for example.

Figure 7:
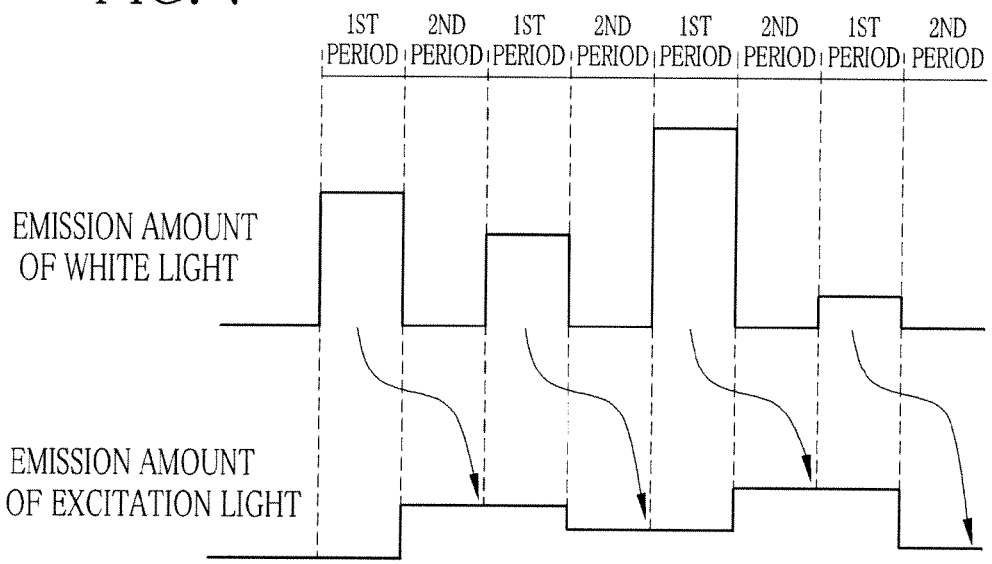
FIG. 7 is an explanatory view of a method for controlling the emission amount of the excitation light in accordance with the emission amount of the white light.

As described above, when the emission amount of the white light is changed, the emission amount of the excitation light is automatically and correspondingly changed. Thus, the exposure balance between the normal image and the special image is always maintained in an appropriate state. Note that, the emission amount of the excitation light may be controlled at switching timing from the first period to the second period so as to have a predetermined correlation between the white light and the excitation light, as shown in FIG. 7, instead of being controlled in conjunction with the control of the emission amount of the white light.

The excitation light from the first excitation light source 72 is incident upon the first optical fiber 38 of the over-tube 13. The excitation light from the second excitation light source 73 is incident upon the second optical fiber 39 of the over-tube 13. Then, referring to FIG. 4, the excitation light transmitted through the first optical fiber 38 is ejected from the first light projection unit 41 of the hood 14. The excitation light transmitted through the second optical fiber 39 is ejected from the second light projection unit 42 of the hood 14.

Figure 8:
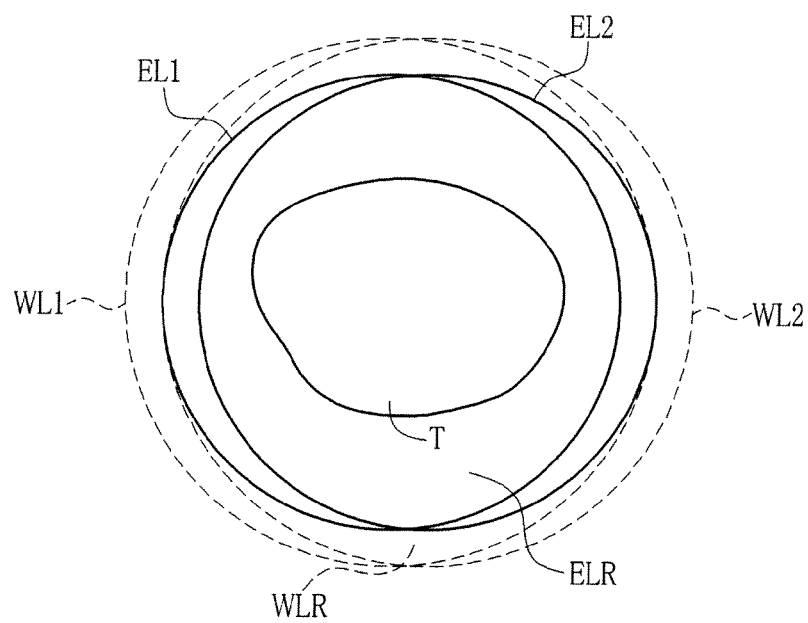
FIG. 8 is an explanatory view of irradiation areas of the excitation light.

As with the first and second lighting windows 57 and 59 provided in the distal end portion 24a, the first and second light projection units 41 and 42 are symmetric with respect to the excitation light cut filter 32 (or the imaging window 62) of the hood 14. As shown in FIG. 8, an irradiation area EL1 of the excitation light emitted from the first light projection unit 41 and an irradiation area EL2 of the excitation light emitted from the second light projection unit 42 overlap each other at an excitation light overlapping area ELR. Furthermore, the excitation light overlapping area ELR is contained in the white light overlapping area WLR at which the two white light irradiation areas WL1 and WL2 overlap.

Since the distal end portion 24a is aimed at the target area T such that the target area T is enclosed within the excitation light overlapping area ELR of the excitation light irradiation areas EL1 and EL2, the target area T is irradiated enough and uniformly with the excitation light. Therefore, if the entire target area T is formed of normal tissue, the autofluorescence is emitted at substantially the same intensity from the entire target area T. Furthermore, since the excitation light overlapping area ELR is contained in the white light overlapping area WLR, the ratio between the white light amount and the excitation light amount is kept at constant throughout the target area T.

Figure 9:
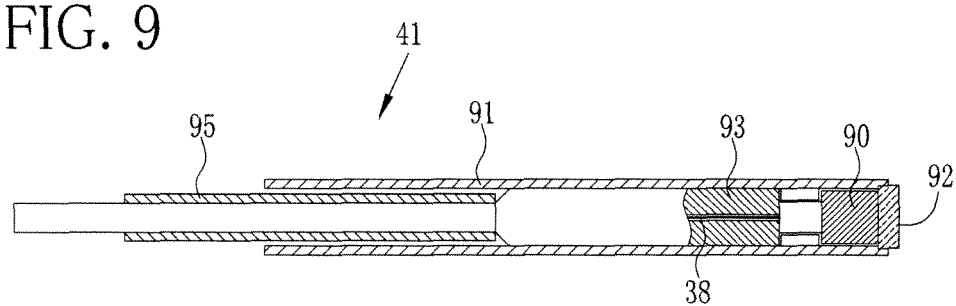
FIG. 9 is a cross sectional view of a first light projection unit for projecting the excitation light.

Referring to FIG. 9, the first light projection unit 41 includes a light diffusing member 90, a tubular sleeve member 91 for covering the periphery of the light diffusing member 90, a protective glass plate 92 for sealing one end of the sleeve member 91, and a ferrule 93 fitted into the sleeve member 91 to hold the first optical fiber 38. The first optical fiber 38 extends from a rear end of the ferrule 93 in a state of being covered with a jacket. The first optical fiber 38 with the jacket is covered with a flexible sleeve 95, which is inserted in the sleeve member 91. Since the configuration of the second light projection unit 42 is the same as that of the first light projection unit 41, the description thereof is omitted.

The light diffusing member 90 is made of a transparent resin material that diffuses the excitation light from the first optical fiber 38. In addition to the transparent resin material, transparent ceramic, glass, or the like is available. The light diffusing member 90 may have a light diffusing layer, which has minute bumps and dips or is made of a mixture of particles with different refractive indexes (such as filler), in its surface or the middle. In another case, the light diffusing member 90 may be made of a semitransparent material. The light diffusing member 90 uniformalizes the emission amount of the excitation light by the action of polarization and diffusion. Thus, the irradiation area EL1 and emission amount of the excitation light projected from the first light projection unit 41 are adjustable by appropriately changing the material and composition of the light diffusing member 90. In another case, the irradiation area EL1 and emission amount of the excitation light projected from the first light projection unit 41 may be adjusted by appropriately changing a lens or the protective glass plate 92, instead of or in addition to changing the material and composition of the light diffusing member 90.

As shown in FIG. 2, the electronic endoscope 11 is provided with the CCD 100, an analog frontend processor (AFE) 104, and an imaging controller 106. The CCD 100 receives on its imaging surface 100a light that has transmitted through the excitation light cut filter 32, the imaging window 62, and a condenser lens 102. The CCD 100 performs photoelectric conversion of the light received on its imaging surface 100a, and accumulates signal charges. The accumulated signal charges are read out as an imaging signal. The readout imaging signal is sent to the AFE 104.

The CCD 100 is a color CCD having three color pixels of R-, G-, and B-pixels with R, G, and B color filters, respectively, arranged in its imaging surface 100a. Since the white light ranges from the blue wavelength band to the red wavelength band, all of the R-, G-, and B-pixels react to the white light incident upon the imaging surface 100a. Thus, the imaging signal obtained in receiving the white light contains an R imaging signal outputted from the R-pixels, a G imaging signal outputted from the G-pixels, and a B imaging signal outputted from the B-pixels.

On the other hand, the autofluorescence is substantially in a green wavelength band, though it partly ranges to the blue or red wavelength band. For this reason, the G-pixels certainly react to the autofluorescence incident upon the imaging surface 100a. In other words, the imaging signal obtained in receiving the autofluorescence contains at least the G imaging signal.

The AFE 104 includes a correlated double sampling circuit (CDS) and an automatic gain controller (AGC). The CDS applies a correlated double sampling process to the imaging signal from the CCD 100, to remove noise, which is caused by the drive of the CCD 100, from the imaging signal. The AGC amplifies the imaging signal after the noise removal by the CDS.

The imaging controller 106 controls the imaging operation of the CCD 100. Following the control by the imaging controller 106, the imaging signal is outputted from the AFE 104 at a predetermined frame rate. The imaging controller 106 is connected to the system controller 113 of the processor device 15. Thus, the imaging controller 106 appropriately changes its control method in accordance with the imaging mode and the like that the system controller 113 recognizes at the time of imaging.

Figure 10A:
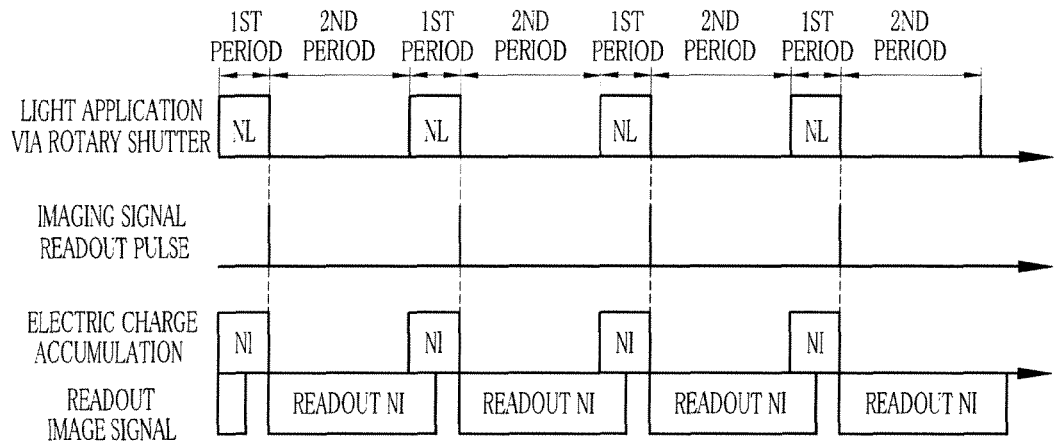
FIG. 10A is an explanatory view of CCD imaging control in a normal imaging mode.

In the normal imaging mode, as shown in FIG. 10A, a normal image capture step (NI) for performing the photoelectric conversion of the white light and accumulating the signal charges is carried out in the first period. Then, in synchronization with a turn from the first period to the second period, an imaging signal readout pulse is sent from the imaging controller 106 to the CCD 100. Upon receiving the imaging signal readout pulse, the signal charges accumulated in the CCD 100 are outputted to the AFE 104 as a normal imaging signal. Then, taking a turn from the second period to the first period, the normal image capture step (NI) is carried out again. The above sequential operation is repeated as long as the electronic endoscope system 10 is set in the normal imaging mode.

Figure 10B:
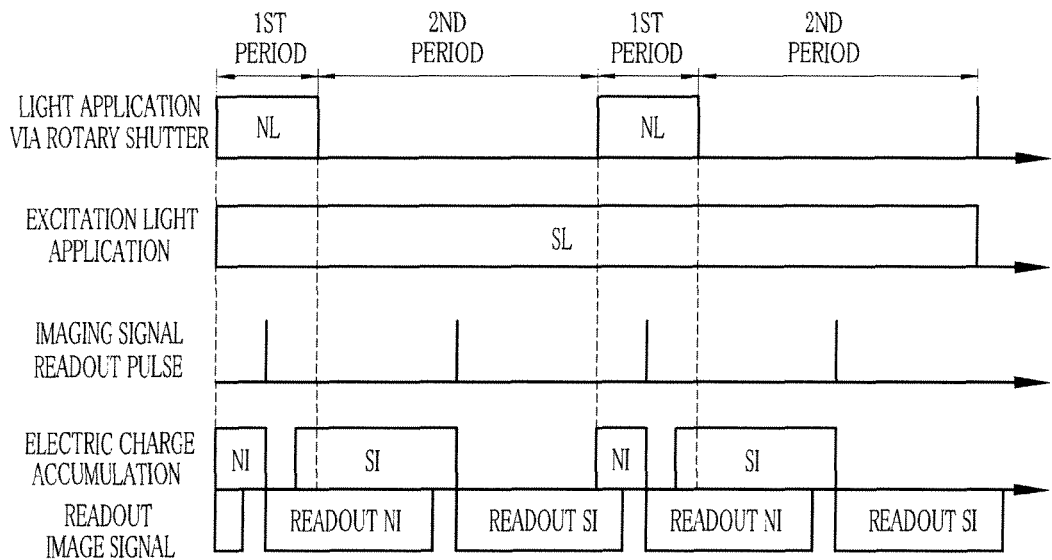
FIG. 10B is an explanatory view of CCD imaging control in a special imaging mode.

In the special imaging mode, on the other hand, as shown in FIG. 10B, the normal image capture step (NI) for performing the photoelectric conversion of the white light and accumulating the signal charges is carried out in a first half of the first period. Then, the imaging signal readout pulse is sent from the imaging controller 106 to the CCD 100 in the middle of the first period. Upon receiving the imaging signal readout pulse, the signal charges accumulated in the CCD 100 are outputted to the AFE 104 as the normal imaging signal. Since the excitation light is always applied, only the autofluorescence is incident on the CCD 100 soon after the start of the readout of the normal imaging signal. Then, the CCD 100 carries out a special image capture step (SI) for performing the photoelectric conversion of the autofluorescence and accumulating the signal charges. Although the intensity of the autofluorescence is weak, the CCD 100 can certainly receive a sufficient amount of the autofluorescence enough to form a special image, because the duration of the second period in the special imaging mode is twice as long as that in the normal imaging mode.

After a lapse of predetermined time from the turn to the second period, the imaging signal readout pulse is sent from the imaging controller 106 to the CCD 100. In response to it, the signal charges accumulated in the CCD 100 are outputted to the AFE 104 as a special imaging signal. On the turn from the second period to the first period, the normal image capture step (NI) is carried out again. The above sequential operation is repeated as long as the electronic endoscope system 10 is set in the special imaging mode.

The processor device 15, as shown in FIG. 2, is electrically connected to the electronic endoscope 11, the normal light source device 16, the special light source device 17, the monitor 18, a keyboard (not shown), a printer (not shown), and the like to perform centralized control of the electronic endoscope system 10. The processor device 15 includes a signal processor 110, a frame memory 112, and the system controller 113.

The signal processor 110, which includes an A/D converter 115, a tone correction section 116, and an image processing section 117, applies various processes to the imaging signal outputted from the AFE 104 of the electronic endoscope 11 to produce a picture signal to be displayed on the monitor 18. Based on this picture signal, images of various types are displayed on the monitor 18. Note that, each of the tone correction section 116 and the image processing section 117 is composed of, for example, a software program for making a computer carry out appropriate processing, a memory device such as an EPROM (erasable programmable ROM) for storing the software program, and the like. The frame memory 112 stores digital image data after the A/D conversion and the picture signal after being processed by the image processing section 117 temporarily or whenever the data or picture signal is updated.

The A/D converter 115 converts the imaging signal from the AFE 104 to the digital image data. The image data contains a B component produced from the B imaging signal, a G component produced from the G imaging signal, and an R component produced from the R imaging signal. The image data after the A/D conversion includes normal image data obtained in both the normal imaging mode and the special imaging mode, and special image data obtained in the special imaging mode.

Figure 11:
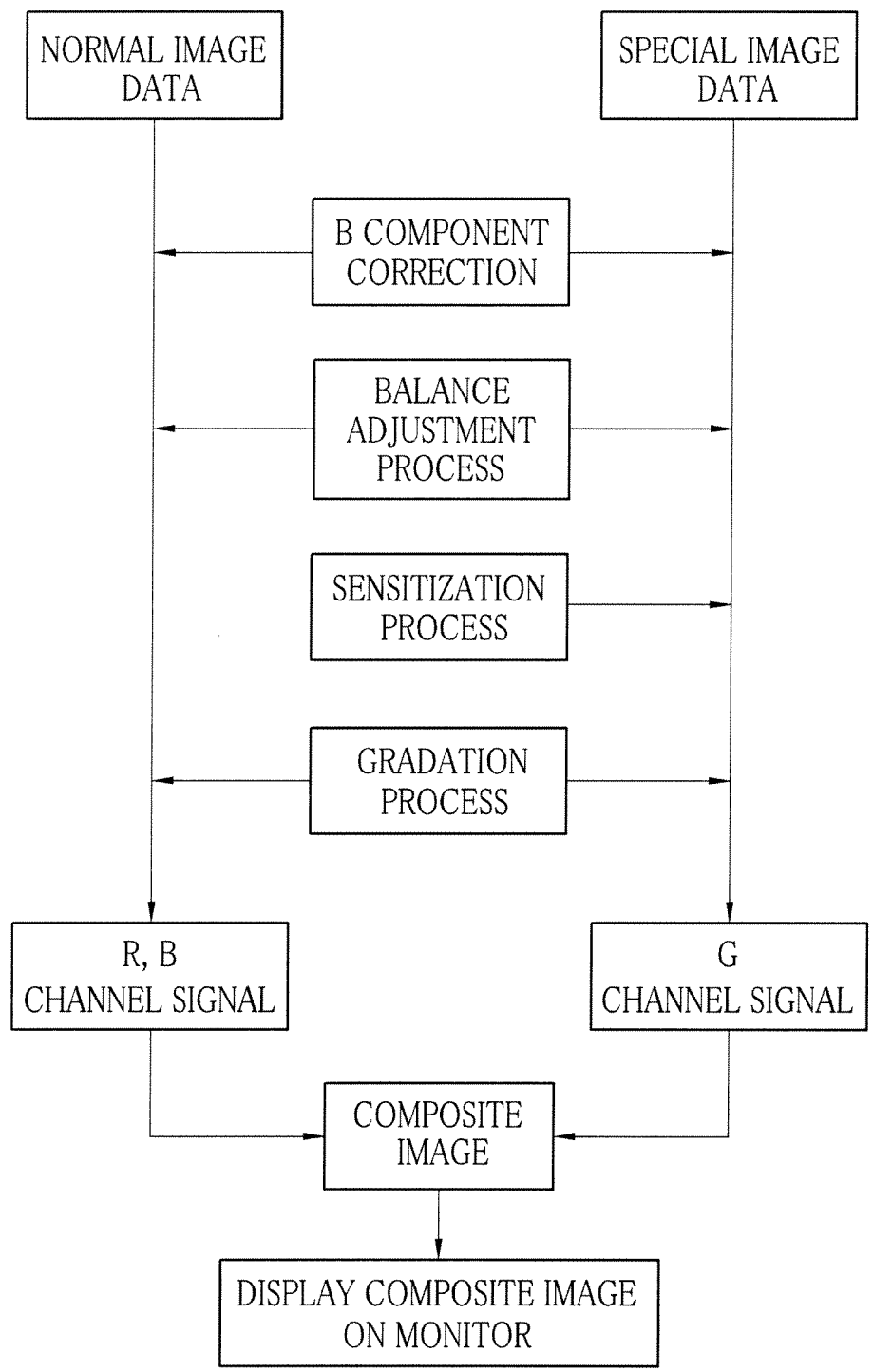
FIG. 11 is an explanatory view of a processing flow of a signal processor.

The tone correction section 116 and the image processing section 117 carry out their operation in accordance with a flow of FIG. 11. The tone correction section 116 compensates for the B component of the normal and special image data, which is partly or totally cut out by the excitation light cut filter 32. As shown in FIG. 3, since the electronic endoscope 11 captures the image through the excitation light cut filter 32 that partly or totally cuts out a light component in a wavelength band of 415 nm or less, the B component of the normal and special image data, being in a short wavelength band, is cut out. The tone correction section 116 corrects this B component.

The B component of the normal image data is corrected as follows. First, the following correction expressions (1) and (2) are calculated in advance. In the expressions (1) and (2), B' represents the intensity of the B component in the normal image data obtained without attaching the excitation light cut filter 32, while B represents the intensity of the B component in the normal image data obtained with attaching the excitation light cut filter 32. The relation between B and B' is expressed by the expression (1).

$$B = B' \times \alpha \quad (1)$$

Wherein, $\alpha$ represents an intensity cut rate by the excitation light cut filter 32. Thereby, B' is calculated by the expression (2).

$$B' = B/\alpha \quad (2)$$

As indicated by the expression (2), when B and B' show a linear relation, the intensity B of the B component in the normal image data obtained with attachment of the excitation light cut filter 32 is divided by a coefficient $\alpha$, to obtain the intensity B' to which the intensity cut by the excitation light cut filter 32 is added. Then, the intensity B of the B component in the normal image data is replaced by the intensity B', in order to obtain a normal image substantially the same as that captured without attachment of the excitation light cut filter 32.

If B and B' show a nonlinear relation, on the other hand, the intensity of the B component may be increased by arithmetic computations such as multiplication, addition, and matrix conversion, for example. The G and R components may be decreased in accordance with the intensity of the B component cut by the excitation light cut filter 32. Furthermore, in a case where a part of the G component on a short wavelength side is cut by the excitation light cut filter 32, the G component is preferably corrected in a like manner.

Referring to FIG. 2, the image processing section 117 includes a balance adjustment section 120, a sensitization section 121, and a gradation processing section 122. In the special imaging mode, the balance adjustment section 120 performs a balance adjustment process between the normal image and the special image using correction data. The correction data is produced from the normal and special images of tumor tissue (a portion where a cancer at an early stage emerges) and normal tissue of an unspecified patient that are captured in advance.

By the balance adjustment process using the correction data, the contrast between the tumor tissue and the normal tissue in the normal image is equalized to that in the special image. Taking a case where the contrast of the special image is one-fifths of the contrast of the normal image as an example, the balance adjustment section 120 multiplies the contrast of the special image by five based on the correction data, as the balance adjustment. Since the ratio between the white light emission amount and the excitation light emission amount is kept at constant, as described above, the balance adjustment is carried out with high precision.

The balance between the normal image and the special image is dependent on the characteristics of the CCD 100 and the like. Accordingly, the function of the balance adjustment is preferably checked at least once before shipment of the electronic endoscope system 10 or before first use of the electronic endoscope system 10.

Figure 12:
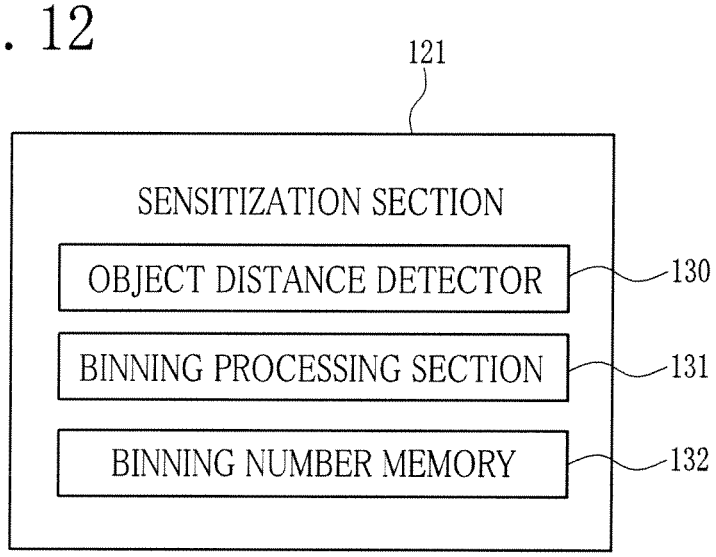
FIG. 12 is a block diagram of a sensitization section.

After that, the sensitization section 121 applies a sensitization process to the special image data. As shown in FIG. 12, the sensitization section 121 includes an object distance detector 130, a binning processing section 131, and a binning number memory 132. The object distance detector 130 detects an exposure amount from the normal image, and calculates an object distance from the distal end portion 24a containing the CCD 100 to the internal body part to be imaged (object) based on the detected exposure amount. Here, the object distance is assumed to be short when the exposure amount is large, while the object distance is assumed to be long when the exposure amount is small. Note that, the object distance may be calculated from the special image.

The binning processing section 131 sensitizes the special image data by application of a software binning process. In the software binning process, adjoining plural pixels are integrated into a single pixel group, and the special image is reconfigured on a pixel group basis. An intensity value of each pixel group refers to an addition of intensity values of all pixels contained in the pixel group. A binning number refers to the number of pixels contained in the single pixel group. The binning number is represented as a multiplication of the number of pixels arranged in a vertical direction and the number of pixels arranged in a horizontal direction, for example, 2×2. The binning number is stored in advance in the binning number memory 132. Note that, the sensitization process may be applied to the normal image data, in addition to the special image data.

The binning processing section 131 carries out two types of processes, that is, an intensity adjustment process for adjusting the intensity value of the special image data by the software binning process, and a resolution adjustment process for adjusting the resolution of the special image data by the software binning process. Which of the intensity adjustment process and the resolution adjustment process is performed depends on operation on a processing type selector 133 (see FIG. 2).

Figure 13:
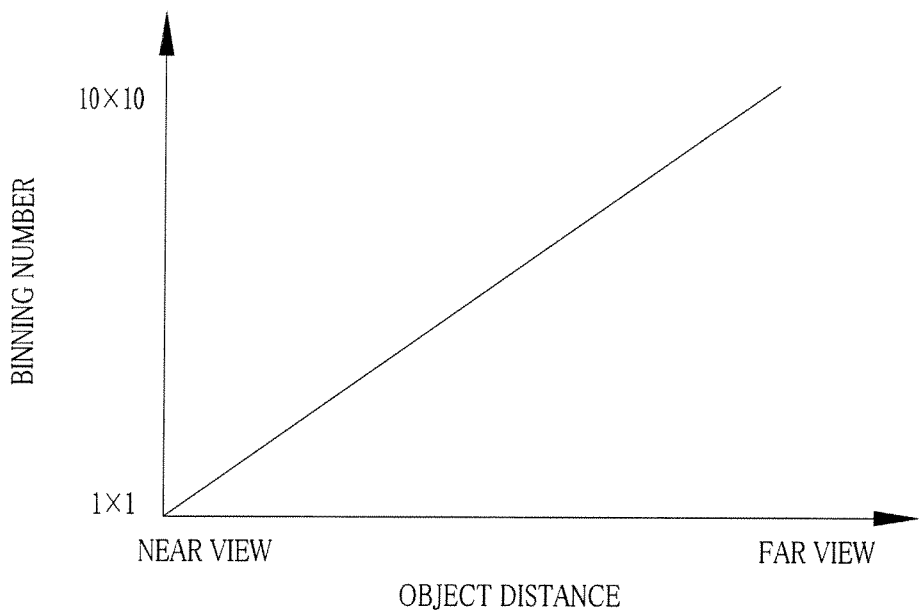
FIG. 13 is a graph showing the relation between a binning number and an object distance in an intensity adjustment process.

In the intensity adjustment process, as shown in FIG. 13, the binning number is set small in a near view having the short object distance. The binning number is increased with increase in the object distance. In a far view having the long object distance, the binning number is maximized. With variation from a near state to a far state, in other words, with increase in the object distance, the special image is increasingly lacking in its intensity. However, the lack of the intensity is eliminated because the binning number is increased in accordance with the increase in the object distance.

In the resolution adjustment process, as shown in FIG. 14, the binning number is set at its maximum in the near view. The binning number is decreased with increase in the object distance. In the far view, the binning number reaches its minimum. An image of the object to be inspected becomes small with varying from the near state to the far state, in other words, with increase in the object distance, resulting in deterioration of the visibility of the object. However, decreasing the binning number and improving the resolution can eliminate the deterioration of the visibility.

In this embodiment, the binning number is increased or decreased in accordance with the object distance. Instead of this, a frame addition process may be performed in accordance with a motion of the object. In the frame addition process, the special image data of continuous plural frames is added to produce the high-quality special image data of a single frame. In this frame addition process, the number of frames of the special image data used for producing the high-quality special image data is changed in accordance with the motion of the object. For example, when the object barely moves, the number of frames is increased to improve the image quality of the produced special image data. When the object actively moves, on the other hand, the number of frames is decreased to prevent the occurrence of blurring in the produced special image data.

The binning number may be changed by calculation using a function shown in a graph of FIG. 13 or 14, or may be changed with the use of a LUT 136 shown in FIG. 15, in which the correspondence between the object distance and the binning number is represented. The sensitization section 121 may decrease the binning number when the object contains high-frequency structure at a high rate, while increase the binning number when the object contains the high-frequency structure at a low rate. When the binning number is large, a high-frequency enhancement process may be carried out. In another case, the binning number may differ between the time of screening and the time of detailed inspection. If the CCD has a high pixel count, the binning process may not be carried out when the high-resolution image is required, though the binning process may be carried out in other cases.

The gradation processing section 122 carries out a gradation process for converting the normal or special image data into the picture signal displayable on the monitor 18. The gradation process includes a gamma correction process and a gradation correction process compatible with the monitor 18. According to the gradation process, in the normal imaging mode, the B component of the normal image data is assigned to a B channel of the picture signal, the G component of the normal image data is assigned to a G channel of the picture signal, and the R component of the normal image data is assigned to an R channel of the picture signal.

In the special imaging mode, on the other hand, the B component of the normal image data is assigned to the B channel of the picture signal, the R component of the normal image data is assigned to the R channel of the picture signal, and a G component of the special image data is assigned to the G channel of the picture signal. Thereby, a composite image of the normal image and the special image is obtained. The autofluorescence emitted from the normal tissue has a high intensity level, while the autofluorescence emitted from the tumor tissue has a low intensity level. Thus, when capturing an image of the normal tissue, the G component of the special image data has a high signal value. On the other hand, when capturing an image of the tumor tissue, the G component of the special image data has a low signal value. Thereby, when the composite image, in which the G component of the special image data is assigned to the G channel, is displayed on the monitor 18, the normal tissue is colored green, while the tumor tissue is colored magenta.

Note that, increase in the object distance becomes one of reasons why the intensity level of the autofluorescence is decreased, besides the presence of the tumor tissue. Thus, the image processing section 117 compares the intensity level between the G component of the normal image data and the G component of the special image data, before displaying the magenta color on the monitor 18. As a result of comparison, if the intensity level is low at both the normal image data and the special image data, it is judged that the decrease in the intensity level is simply caused by the far object distance. A portion with the low intensity level is displayed with green, instead of magenta. If the intensity level of the G component of the normal image data is high while that of the special image data is low, on the other hand, a portion with the low intensity level is judged to be the tumor tissue, and displayed with magenta.

Next, the operation of the present invention will be described. First, the electronic endoscope system 10 is set to the special imaging mode by operation on the imaging mode switching button 28. In the special imaging mode, the white light and the excitation light are applied to the internal body part in the first period, and only the excitation light is applied thereto in the second period. Since the excitation light is applied continuously in both the first and second periods, the autofluorescence is invariably emitted from the living body tissue inside the body cavity. Then, the electronic endoscope 11 captures the normal image in the first period, and captures the special image mostly in the second period using the CCD 100. The captured normal and special imaging signals are sent to the processor device 15.

In the processor device 15, the A/D converter 115 converts each imaging signal into the digital image data. Then, the tone correction section 116 applies the tone correction process to the obtained image data, and the balance adjustment section 120 of the image processing section 117 applies the balance adjustment process using the correction data. After that, the sensitization section 121 applies the sensitization process, and the gradation processing section 122 applies the gradation process. Through these processes, the composite image of the normal image and the special image is obtained. The composite image is displayed on the monitor 18.

The sensitization section 121 of the image processing section 117 performs the sensitization process of the special image data by applying the software binning process to the special image. First, the object distance detector 130 detects the object distance based on the normal image data. After that, the binning processing section 131 increases or decreases the binning number in accordance with the object distance.

In the intensity adjustment mode, as shown in FIG. 13, the binning number is increased with increase in the object distance. This eliminates the lack of the intensity caused by change from the near state to the far state. In the resolution adjustment mode, on the other hand, as shown in FIG. 14, the binning number is decreased with increase in the object distance, to improve the resolution. The improvement of the resolution prevents the deterioration in the visibility of the object, which occurs in the far state.

In the above embodiment, the software binning process to be applied to the normal image data sent from the electronic endoscope 11 to the processor device 15 is carried out. Instead of this, a hardware binning process to be performed by the CCD 100 of the electronic endoscope 11 may be carried out. In the hardware binning process, when the signal charges are read out from the CCD 100, the signal charges of the adjoining plural pixels are added together. The added signal charges are outputted as the imaging signal of the single pixel group. The number of pixels contained in the pixel group is reduced when the object moves little, while the number of pixels contained in the pixel group is increased when the object moves largely.

Second Embodiment

Figure 16:
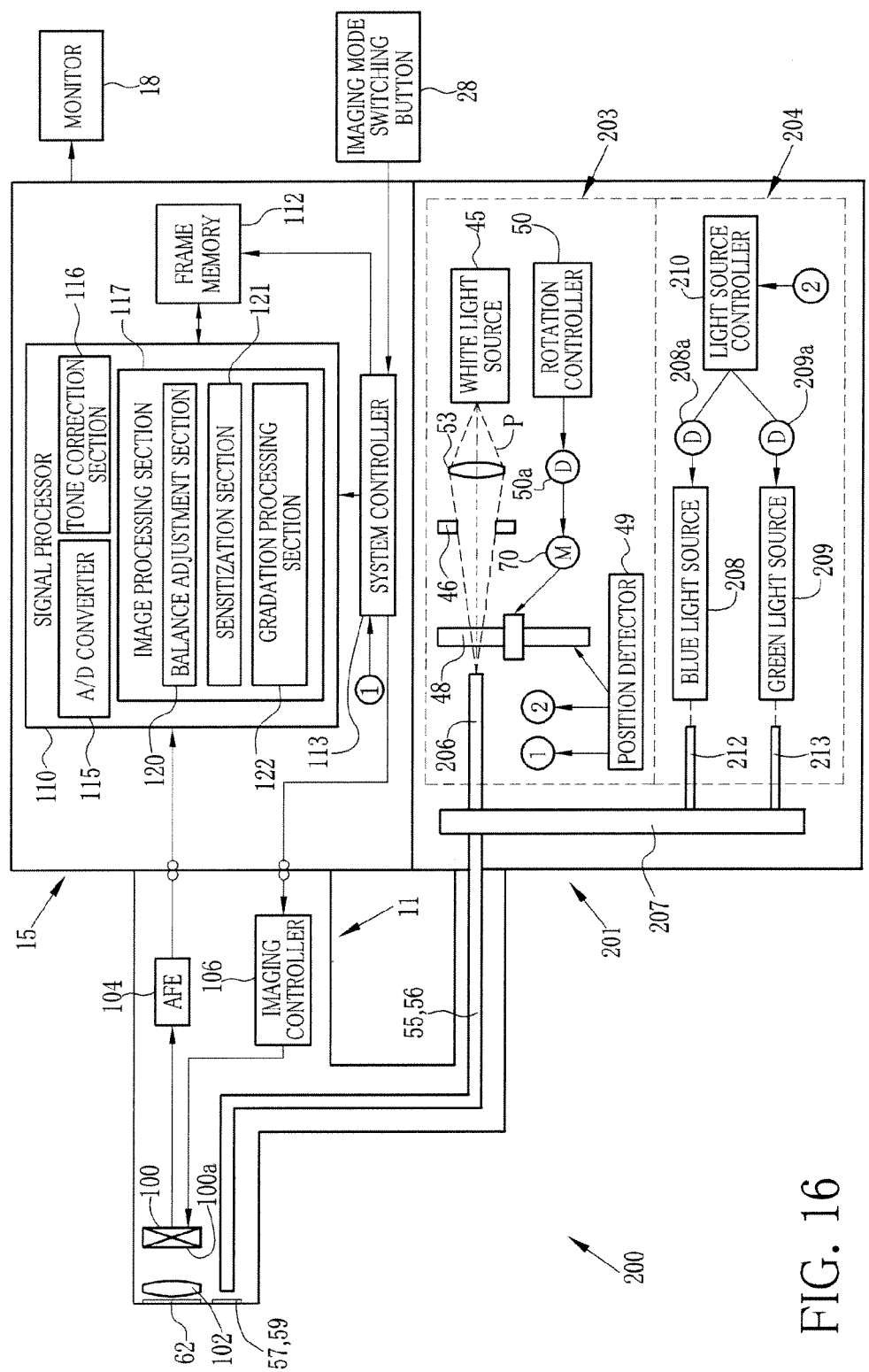
FIG. 16 is a block diagram showing an electronic endoscope system according to a second embodiment.

In a second embodiment of the present invention, an electronic endoscope system 200, as shown in FIG. 16, carries out narrow band imaging (NBI) in which narrow band light is applied to the internal body part to display a superficial blood vessel with enhancement. The structure of the electronic endoscope system 200 according to the second embodiment is partly different from that of the electronic endoscope system 10 of the first embodiment.

The electronic endoscope system 200 is provided with an NBI-specific light source device 201, instead of the normal light source device 16 and the special light source device 17 of the first embodiment. In the electronic endoscope system 200, in contrast to the first embodiment, the hood 14 having the excitation light cut filter 32 and the first and second light projection units 41 and 42 is not attached to the distal end portion 24a of the electronic endoscope 11, and the over-tube 13 containing the optical fibers 38 and 39 is not disposed through the insert section 20. Also, in the electronic endoscope system 200, the sensitization section 121 and the gradation processing section 122 of the processor device 15 carry out NBI-specific processes. The other components of the electronic endoscope system 200 are the same as those of the electronic endoscope system 10.

The NBI-specific light source device 201 includes a normal light source unit 203 and a special light source unit 204. The normal light source unit 203 has structure similar to the normal light source device 16 of the first embodiment. White light (normal light) from the normal light source unit 203 is incident upon an optical fiber 206 in the first period. The white light transmits through the optical fiber 206, and is incident upon the light guides 55 and 56 through a coupler 207.

The special light source unit 204 includes a blue light source 208 for emitting NBI-specific blue light in a specific narrow wavelength band out of a blue wavelength band, a green light source 209 for emitting NBI-specific green light in a specific narrow wavelength band out of a green wavelength band, and a light source controller 210 for controlling these light sources 208 and 209 via drives 208a and 209a, respectively. It is preferable that the NBI-specific blue light is narrow band light and has a center wavelength of 415 nm, and the NBI-specific green light is narrow band light and has a center wavelength of 540 nm.

The blue light emitted from the blue light source 208 is incident upon an optical fiber 212. The green light emitted from the green light source 209 is incident upon an optical fiber 213. The light transmits through the optical fibers 212 and 213, and is incident upon the light guides 55 and 56 through the coupler 207. The light source controller 210 is connected to the position detector 49 of the normal light source unit 203, and controls the blue and green light sources 208 and 209 in the second period such that each of the blue and green light is applied for predetermined time.

In the first period, the electronic endoscope 11 captures an image of the internal body part irradiated with the white light to take the normal image. In the second period, on the other hand, the electronic endoscope 11 captures an image of the internal body part irradiated with the blue light to take a blue special image, and captures an image of the internal body part irradiated with the green light to take a green special image. The images taken by the electronic endoscope 11 are sent to the processor device 15.

Figure 17:
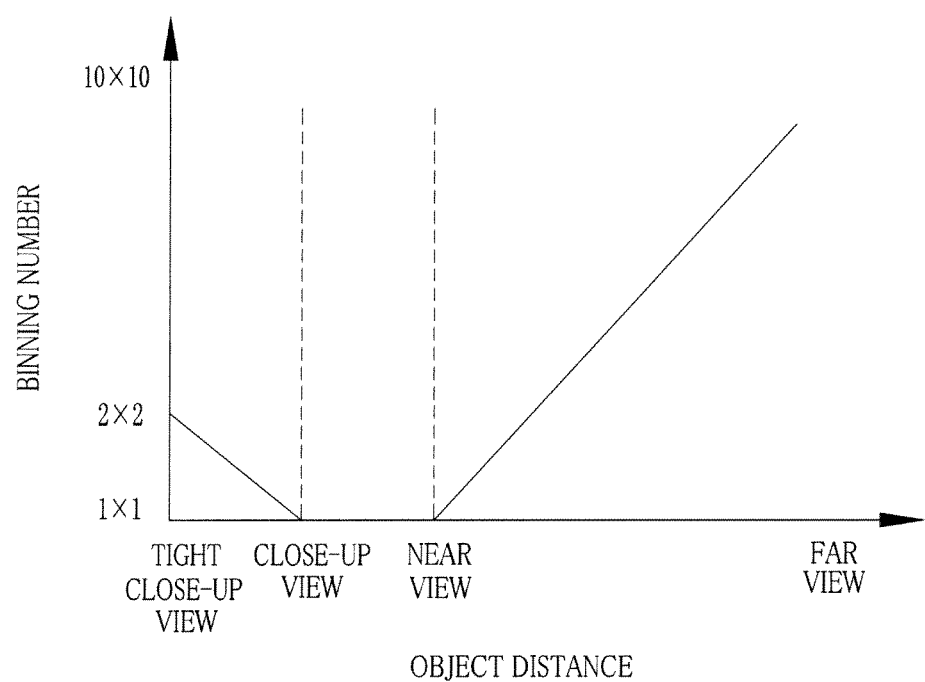
FIG. 17 is a graph showing the relation between the binning number and the object distance in a binning process according to the second embodiment.

The image processing section 117 of the processor device 15 carries out the balance adjustment process as in the case of the first embodiment. The image processing section 117 also carries out an NBI-specific sensitization process and an NBI-specific gradation process. The sensitization section 121 sets a small binning number in the near view, and increases the binning number with increase in the object distance, as shown in FIG. 17. The binning number is maximized in the far view. When the object is inspected in more detail, so-called magnification imaging is carried out. In the magnification imaging, the distal end portion 24a of the insert section 20 is brought nearer to the object than the near state (i.e. the object distance is shortened), and a magnified image of the object is captured. By the magnification imaging, two types of views including a tight close-up view and a close-up view are capturable depending on the object distance. In the tight close-up view, the distal end portion 24a is brought into a tight close-up state with the nearest possible object distance, and an image is captured in that state. In the close-up view, the distal end portion 24a is brought into a close-up state being farther from the object than the tight close-up state (i.e. the object distance is a little longer than that of the tight close-up state) though is still nearer to the object than the near state. The binning number is slightly increased in the tight close-up state, as compared with the binning number set between the close-up state and the near state. For example, the binning number in the tight close-up state is set at 2×2, while the binning number between the close-up state and the near state is set at 1×1.

Note that, a technique of varying the binning number between the close-up state and the tight close-up state may be adopted in a magnification endoscope equipped with a zoom function. In this case, a low magnified state refers to a state in which an image is captured with slightly increasing a magnifying power with the object distance set at the near state, and a high magnified state refers to a state in which an image is captured with further increasing the magnifying power with the object distance set at the near state. The binning number is increased in the high magnified state than that in the low magnified state, just as in the case of the tight close-up state and the close-up state.

In the NBI, increasing the binning number eliminates the lack of the intensity that is caused by increase in the object distance. Especially, in the NBI, by eliminating the lack of the intensity in the distant view, a brownish area indicating a clot in a blood vessel is easily found out. Furthermore, since the binning number is set slightly larger in the tight close-up view than that in the close-up view, even the minute structure of the object is sharply observable.

When using the NBI function, the gradation processing section 122 assigns the blue special image to the B and G channels of the picture signal, and assigns the green special image to the R channel of the picture signal. Thus, a composite image of the blue special image and the green special image is obtained. In this composite image, the superficial blood vessel is distinguished from the other tissue.

Third Embodiment

Figure 18:
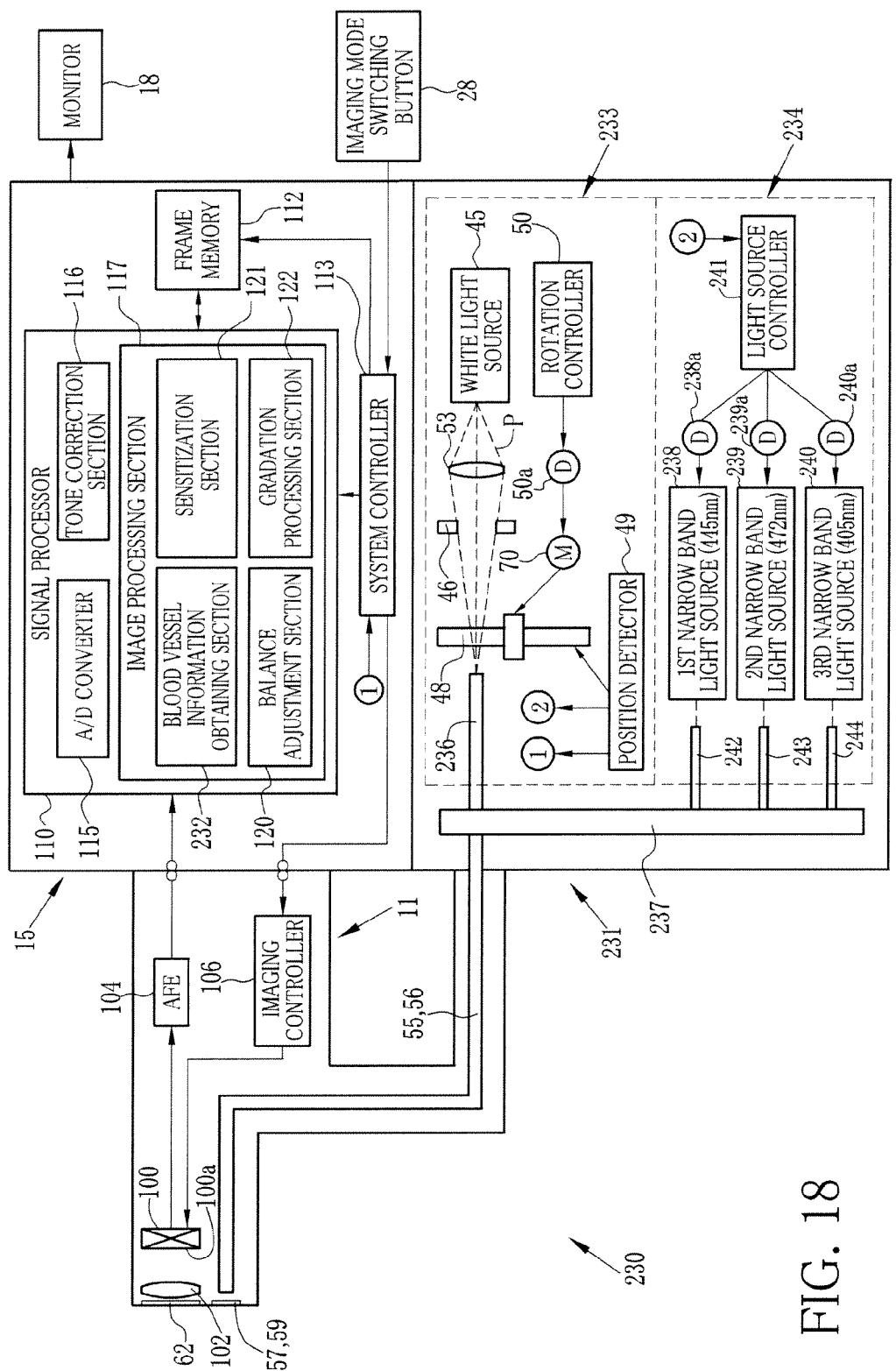
FIG. 18 is a block diagram showing an electronic endoscope system according to a third embodiment.

An electronic endoscope system 230 according to a third embodiment, as shown in FIG. 18, has the function of obtaining blood vessel information related to the depth of a blood vessel and blood oxygen saturation inside the body cavity. The structure of the electronic endoscope system 230 according to the third embodiment is partly different from that of the electronic endoscope system 10 of the first embodiment.

The electronic endoscope system 230 is provided with a light source device 231 for blood vessel information obtainment, instead of the normal light source device 16 and the special light source device 17 of the first embodiment. In the electronic endoscope system 230, in contrast to the first embodiment, the hood 14 having the excitation light cut filter 32 and the first and second light projection units 41 and 42 is not attached to the distal end portion 24a of the electronic endoscope 11, and the over-tube 13 containing the optical fibers 38 and 39 is not disposed through the insert section 20. In the electronic endoscope system 230, the processor device 15 has a blood vessel information obtaining section 232, and the sensitization section 121 and the gradation processing section 122 of the processor device 15 carry out a process corresponding to the blood vessel information obtaining function. The other components of the electronic endoscope system 230 are the same as those of the electronic endoscope system 10.

The light source device 231 includes a normal light source unit 233 and a special light source unit 234 for obtaining the blood vessel information. The normal light source unit 233 has the same structure as that of the normal light source device 16 of the first embodiment. White light (normal light) from the normal light source unit 233 is incident upon an optical fiber 236 in the first period. The white light transmits through the optical fiber 236, and is incident upon the light guides 55 and 56 through a coupler 237.

The special light source unit 234 includes a first narrow band light source 238, a second narrow band light source 239, a third narrow band light source 240, and a light source controller 241. The first narrow band light source 238 emits first narrow band light having a center wavelength of 445 nm. The second narrow band light source 239 emits second narrow band light having a center wavelength of 472 nm. The third narrow band light source 240 emits third narrow band light having a center wavelength of 405 nm. The light source controller 241 controls these light sources 238 to 240 via drivers 238a to 240a, respectively.

The first to third narrow band light emitted from the first to third narrow band light sources 238 to 240 are incident upon optical fibers 242 to 244, respectively. The light transmits through the optical fibers 242 to 244, and is incident upon the light guides 55 and 56 thorough the coupler 237. The light source controller 241 is connected to the position detector 49 of the normal light source unit 233, and controls the first to third narrow band light sources 238 to 240 such that each of the first to third narrow band light is applied for predetermined time in the second period.

The electronic endoscope 11 captures an image of the internal body part irradiated with the white light in the first period to obtain the normal image. In the second period, on the other hand, the electronic endoscope 11 captures an image of the internal body part irradiated with the first to third narrow band light to obtain first to third special images, respectively. The images obtained by the electronic endoscope 11 are sent to the processor device 15.

The image processing section 117 of the processor device 15 carries out the balance adjustment process, just as with the first embodiment, and then carries out the sensitization process corresponding to the blood vessel information obtainment function. The sensitization section 121 applies to the first to third special images the same sensitization process as that of the second embodiment for the NBI. In other words, as shown in FIG. 17, the binning number is set small in the near state, and is increased with increase in the object distance. The binning number is maximized in the far state. In the close-up state having the object distance shorter than that in the near state, the binning number is slightly increased with decrease in the object distance.

In the third embodiment, the blood vessel has to be sharply displayed in the image to obtain from the first to third special images two types of blood vessel information, that is, the depth of the blood vessel and the blood oxygen saturation. Thus, the application of the binning process, just as with the second embodiment for the NBI, allows obtainment of the blood vessel information with high precision.

Figure 19:
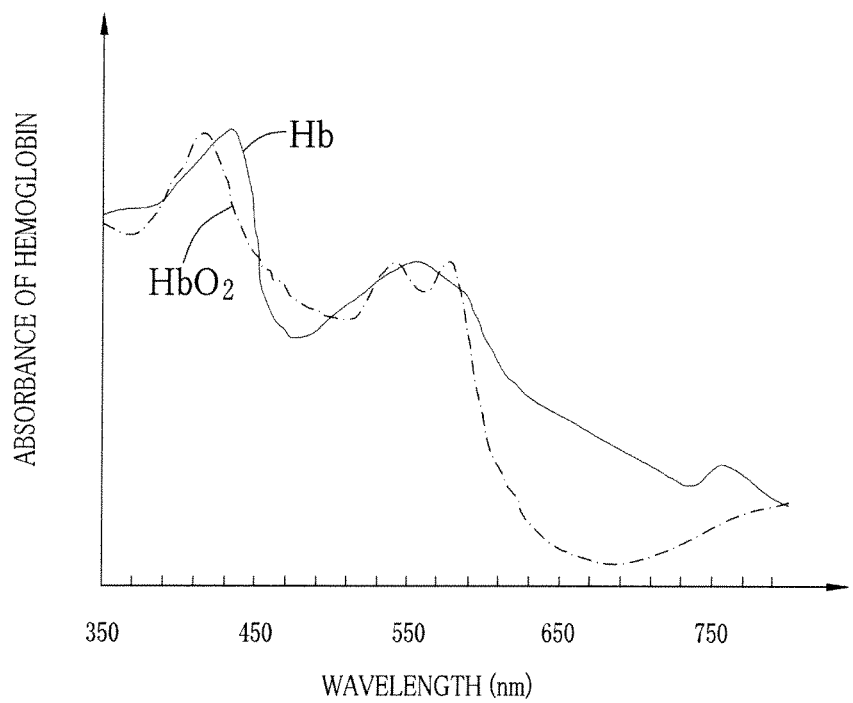
FIG. 19 is a graph showing the light absorbing property of oxygenated hemoglobin and reduced hemoglobin.

The blood vessel information obtaining section 232 obtains from the first to third special images the two types of blood vessel information including the depth of the blood vessel and the blood oxygen saturation. This blood vessel information is obtained by taking advantage of difference in the absorption spectrum between oxygenated hemoglobin $HbO_2$ and the reduced hemoglobin Hb after releasing oxygen, out of hemoglobin contained in a red blood cell in the blood vessel. As shown in FIG. 19 of the spectral characteristic of absorbance, the absorbance of the oxygenated hemoglobin $HbO_2$ is approximately the same as that of the reduced hemoglobin Hb around 405 nm being the center wavelength of the third narrow band light. The absorbance of the reduced hemoglobin Hb is higher than that of the oxygenated hemoglobin $HbO_2$ around 445 nm being the center wavelength of the first narrow band light. The absorbance of the oxygenated hemoglobin $HbO_2$ is higher than that of the reduced hemoglobin Hb around 472 nm being the center wavelength of the second narrow band light. The longer the wavelength of light, the deeper the light transmits into a surface of the living body tissue.

Taking advantage of these properties, the two types of blood vessel information, namely, the depth of the blood vessel and the blood oxygen saturation are obtained. To be more specific, the blood vessel information is obtained by the following steps (A) to (C).

Figure 20:
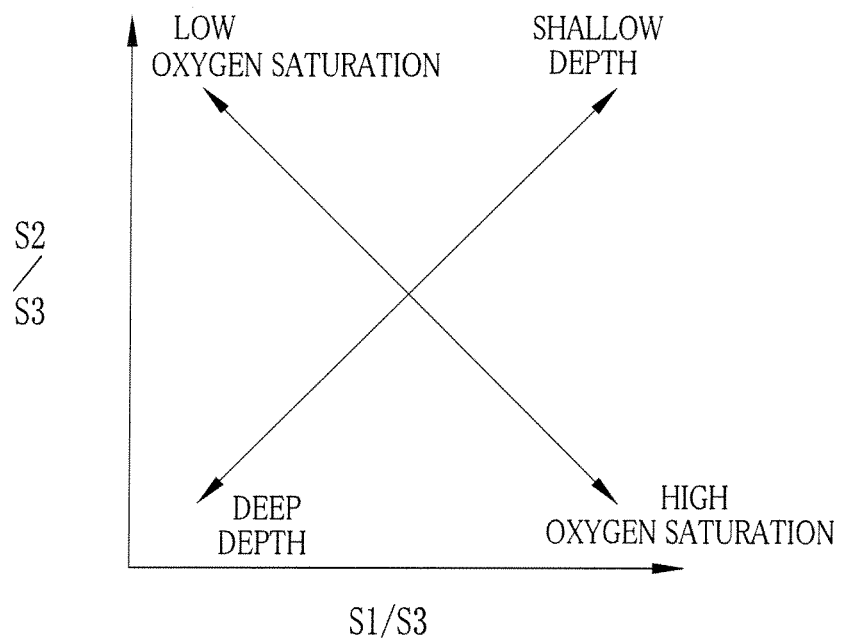
FIG. 20 is a graph showing a two-dimensional map of intensity and blood vessel information.

(A) Intensity values S1 to S3 are obtained from the first to third special images, respectively.
(B) The value S1 is standardized by the value S3. The value S2 is standardized by the value S3. In other words, S1/S3 and S2/S3 are obtained.
(C) A two-dimensional map as shown in FIG. 20 is produced, in which a scale of S1/S3 and a scale of S2/S3 are represented by orthogonal two axes. Then, the obtained values S1/S3 and S2/S3 are plotted on the two-dimensional map. According to the map, the larger the value S1/S3, the shallower the depth of the blood vessel becomes, and the higher the blood oxygen saturation becomes. The smaller the value S1/S3, the deeper the depth of the blood vessel becomes, and the lower the blood oxygen saturation becomes. Also, the larger the value S2/S3, the shallower the depth of the blood vessel becomes, and the lower the blood oxygen saturation becomes. The smaller the value S2/S3, the deeper the depth of the blood vessel becomes, and the higher the blood oxygen saturation becomes. Using this correlation, the information about the blood oxygen saturation and the depth of the blood vessel is obtained.

In using the function of obtaining the blood vessel information, the gradation processing section 122 adds artificial colors to the normal image in accordance with the levels of the blood oxygen saturation and the depth of the blood vessel obtained by the blood vessel information obtaining section 232. The normal image with the artificial colors can notify a radiologist or doctor at sight about the levels of the blood oxygen saturation and the depth of the blood vessel. In this embodiment, the third special image is obtained using the third narrow band light having the wavelength of an equal absorbance point, at which absorbance of HbO and $HbO_2$ is almost equal, and the intensity value S3 obtained from the third special image is used for standardization of S1 and S2. However, the intensity value S3 used in the standardization may not correspond to the equal absorbance point as long as the intensity value is detectable. The intensity values S2 and S3 are obtained using the narrow band light having the two wavelengths between which the magnitude relation of the absorbance between Hb and $HbO_2$ is opposite to each other. However, the magnitude relation may not be opposite between the two wavelengths, as long as the absorbance of Hb and $HbO_2$ differs at the two wavelengths.

Fourth Embodiment

Figure 21:
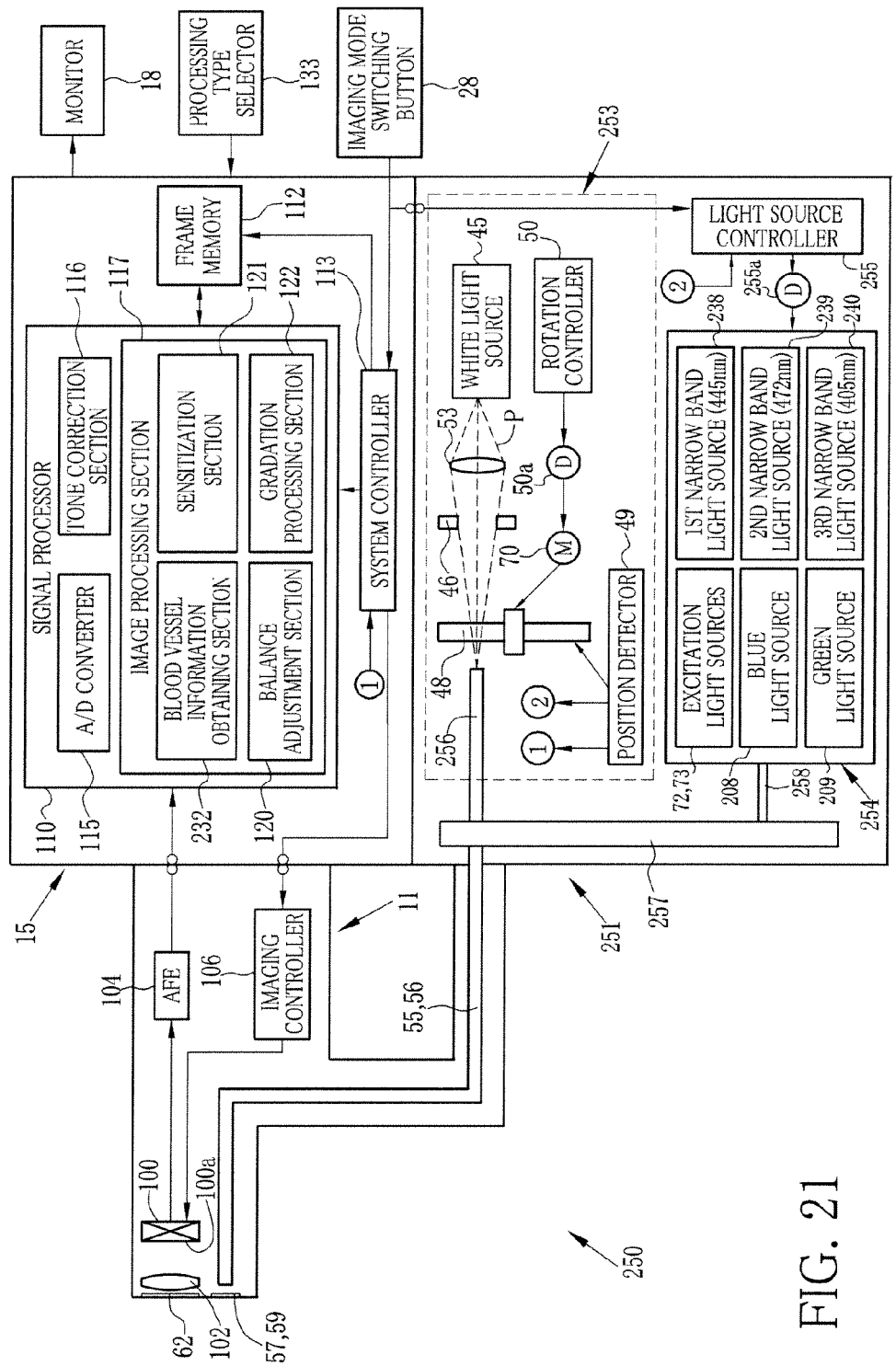
FIG. 21 is a block diagram of an electronic endoscope system according to a fourth embodiment.

As shown in FIG. 21, an electronic endoscope system 250 according to a fourth embodiment of the present invention has three functions of the AFI, the NBI, and obtaining the blood vessel information. The structure of the electronic endoscope system 250 according to the fourth embodiment is partly different from that of the electronic endoscope system 10 of the first embodiment.

The electronic endoscope system 250 is provided with a multi-functional light source device 251, instead of the normal light source device 16 and the special light source device 17 of the first embodiment. In the electronic endoscope system 250, in contrast to the first embodiment, the hood 14 having the excitation light cut filter 32 and the first and second light projection units 41 and 42 is not attached to the distal end portion 24a of the electronic endoscope 11, and the over-tube 13 containing the optical fibers 38 and 39 is not disposed through the insert section 20. In the electronic endoscope system 250, the processor device 15 has the blood vessel information obtaining section 232. The sensitization section 121 and the gradation processing section 122 of the processor device 15 carry out processes corresponding to the AFI, the NBI, and the blood vessel information obtaining function. The other components of the electronic endoscope system 250 are the same as those of the electronic endoscope system 10.

The multi-functional light source device 251 includes a normal light source unit 253, a special light source unit 254, and a light source controller 255. The normal light source unit 253 has the same structure as that of the normal light source device 16 of the first embodiment. White light (normal light) from the normal light source unit 253 is incident upon an optical fiber 256 in the first period. The white light transmits through the optical fiber 256, and is incident upon the light guides 55 and 56 through a coupler 257.

The special light source unit 254 includes the first and second excitation light sources 72 and 73 being the same as those of the first embodiment, the blue and green light sources 208 and 209 being the same as those of the second embodiment, and the first to third narrow band light sources 238 to 240 being the same as those of the third embodiment. The light source controller 255 is connected to the imaging mode switching button 28, and switches among the light sources 72, 73, 208, 209, and 238 to 240 contained in the special light source unit 254 in response to the imaging mode set up by the imaging mode switching button 28. In the fourth embodiment, the special imaging mode includes an AFI mode, an NBI mode, and a blood vessel information obtaining mode. The light source controller 255 is connected to the position detector 49, and controls each light source contained in the special light source unit 254 such that light corresponding to the set imaging mode is appropriately applied in the second period.

Thereby, in the AFI mode, the excitation light is emitted from the first and second excitation light sources 72 and 73. In the NBI mode, the NBI-specific blue light is emitted from the blue light source 208, and the NBI-specific green light is emitted from the green light source 209. In the blood vessel information obtaining mode, the first to third narrow band light is emitted from the first to third narrow band light sources 238 to 240, respectively. The light from the special light source unit 254 is incident upon the light guides 55 and 56 through an optical fiber 258 and the coupler 257. The light source controller 255 controls the emission amount of the light from each light source contained in the special light source unit 254 via a driver 255a.

The processor device 15 carried out processes corresponding to each imaging mode. In other words, in the AFI mode, the processes described in the first embodiment are carried out. In the NBI mode, the processes described in the second embodiment are carried out. In the blood vessel information obtaining mode, the processes described in the third embodiment are carried out. In the fourth embodiment, since the excitation light cut filter 32 is not attached to the distal end portion 24a of the electronic endoscope 11, an anti-halation process is preferably carried out in the AFI mode to prevent the occurrence of the halation due to the application of the excitation light.

Figure 22:
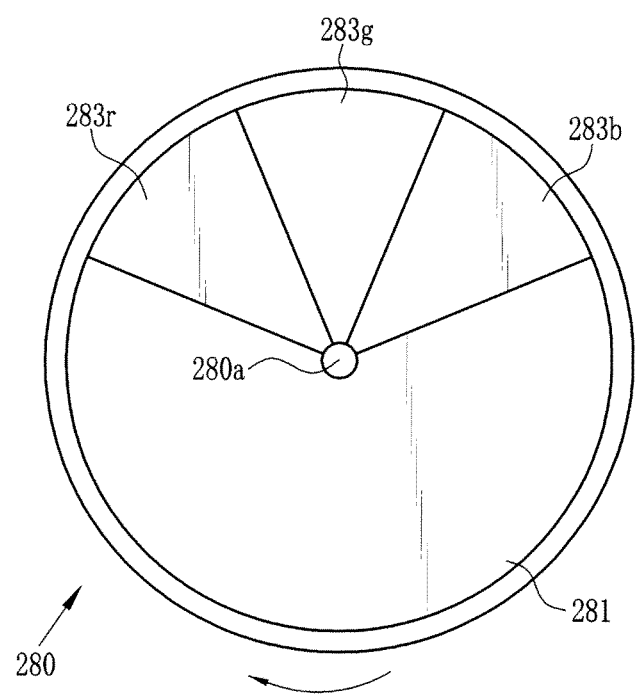
FIG. 22 is a plan view of a rotary filter according to a modification example of the first embodiment.

In the above first embodiment, the white light is applied to the internal body part, but frame sequential light including R, G, and B light may be applied instead. To apply the frame sequential light, a rotary filter 280 shown in FIG. 22 is used instead of the rotary shutter 48 shown in FIGS. 6A and 6B. The rotary filter 280 is constituted of a light shielding portion 281 being similar to the light shielding portion 48b of the rotary shutter 48, an R color filter 283r for transmitting the R light out of the white light emitted from the normal light source 45, a G color filter 283g for transmitting the G light, and a B color filter 283b for transmitting the B light, which are disposed along its circumferential direction. By a turn of the rotary filter 280 around a rotation axis 280a, the R light, the G light, and the B light is applied in this order in the first period.

Figure 23:
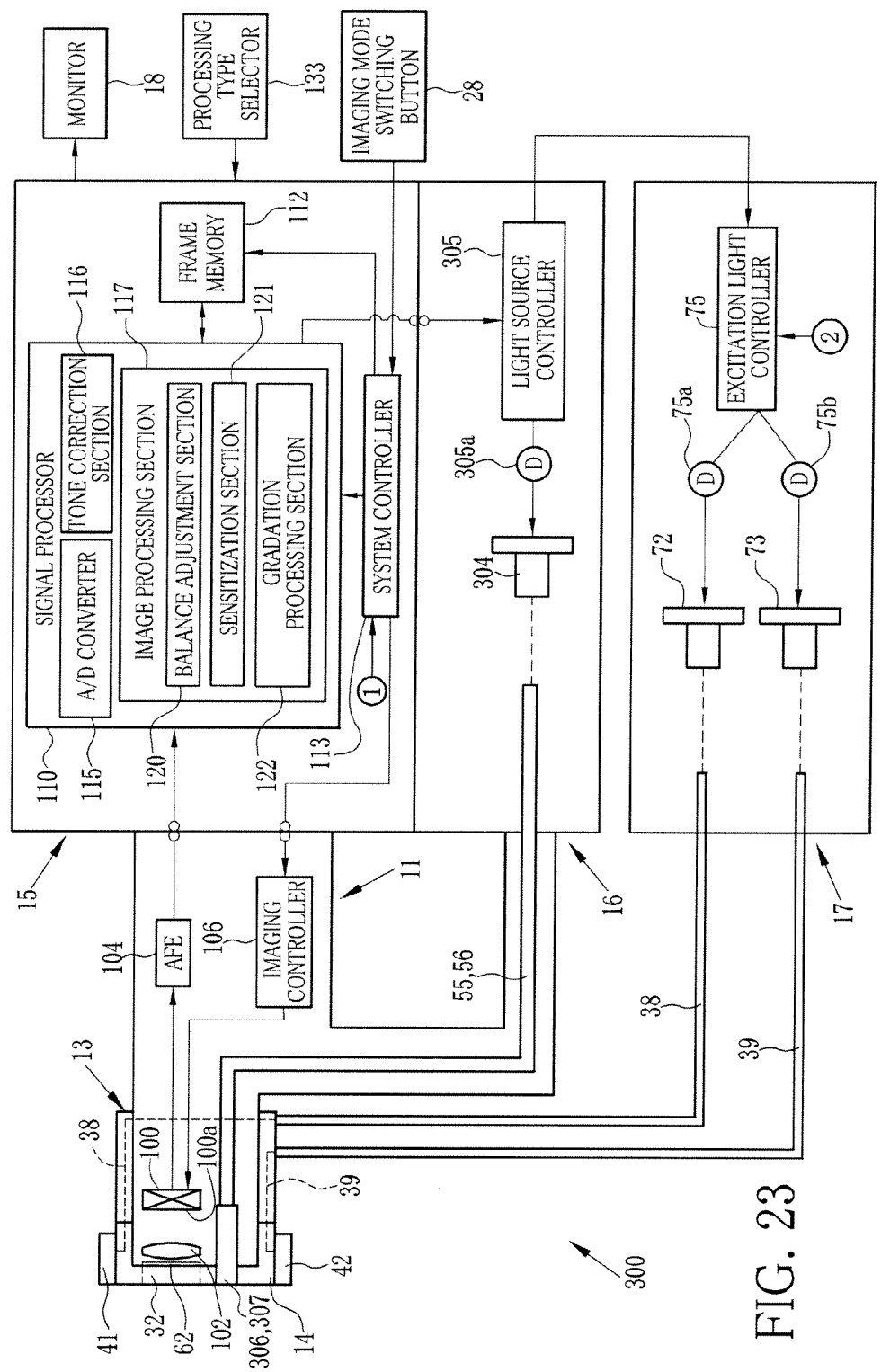
FIG. 23 is a block diagram of an electronic endoscope system according to another modification example of the first embodiment.

In the above first embodiment, the white light source 45 in the normal light source unit 16 produces the white light to be applied to the internal body part. Instead of this, as shown in an electronic endoscope system 300 of FIG. 23, the white light may be produced by a blue excitation light source 304 provided in the normal light source unit 16 and light projection units 306 and 307 provided in the distal end portion 24a of the electronic endoscope 11. The blue excitation light source 304 emits blue laser light having a center wavelength of 445 nm. The emitted blue laser light transmits through the light guides 55 and 56, and is applied to the internal body part through the light projection unit 306 and 307, respectively. Note that, the blue excitation light source 304 is controlled by a light source controller 305 via a driver 305a.

Figure 24:
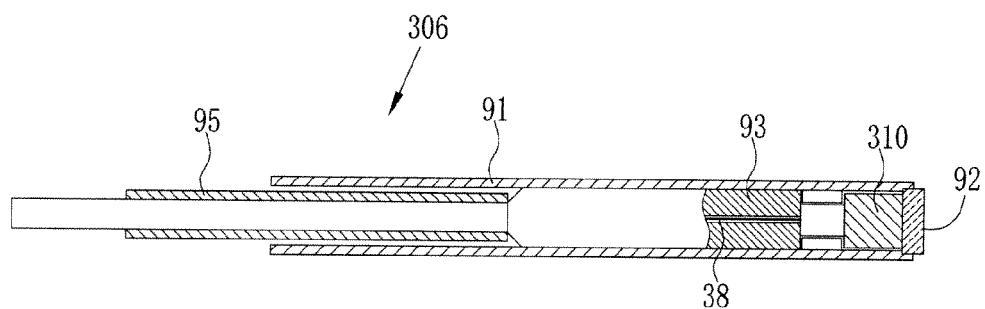
FIG. 24 is a cross sectional view of a normal light projection unit of FIG. 23.

As shown in FIG. 24, the light projection unit 306 has the same structure as those of the first and second light projection units 41 and 42, except for having a phosphor 310 instead of the light diffusing member 90. The phosphor 310 contains plural types of fluorescent materials (for example, a YAG phosphor or a BAM ($BaMgAl_{10}O_{17}$) phosphor) that absorb part of the blue laser light from the light guide 55 and emit green to yellow pumped light.

Thus, the white light is produced by the combination of the green to yellow pumped light, which is emitted in response to the blue laser light as excitation light, and the blue laser light transmitted through the phosphor 310 without being absorbed. The light projection unit 307 has the same structure as that of the light projection unit 306, and detailed description thereof is omitted.

Figure 25:
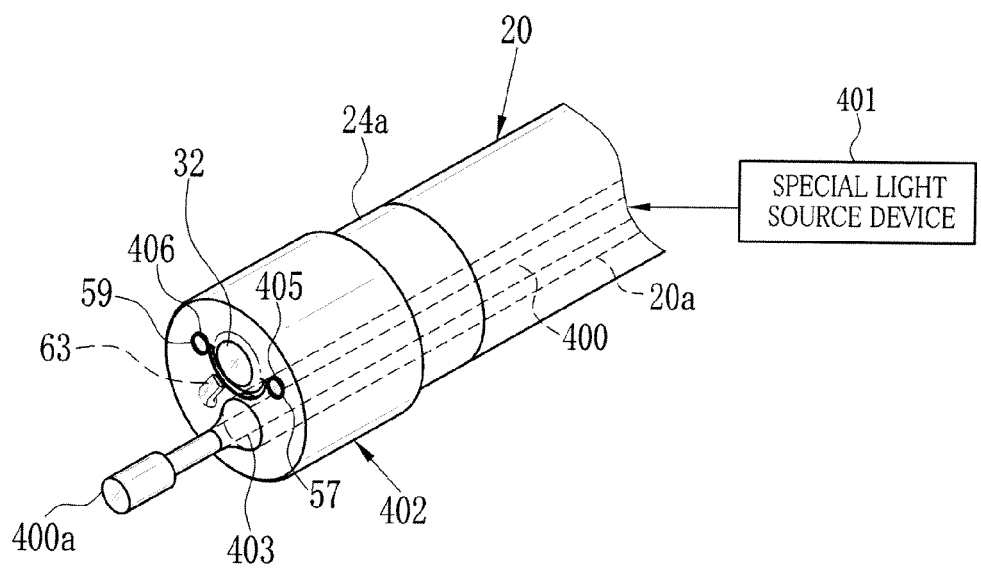
FIG. 25 is a perspective view of a special light probe, a hood, and a distal end portion of an insert section according to further another modification example of the first embodiment.

In the above first embodiment, the excitation light is applied from the first and second light projection units 41 and 42 attached to the hood 14. Instead of this, as shown in FIG. 25, the excitation light may be applied from a light projection section 400a of a probe 400, which is disposed through the medical instrument insertion channel 20a of the insert section 20 and protruded from a probe holder 403 of a hood 402. Note that, the probe 400 is connected to a special light source device 401 having the first and second excitation light sources 72 and 73, which are the same as those of the above embodiments.

The hood 402 has the excitation light cut filter 32 as with the hood 14 of the above embodiments, but is different from the hood 14 in terms of having openings 405 and 406 for exposing the first and second lighting windows 57 and 59. Accordingly, the light projection section 400a of the probe 400 held by the probe holder 403 is aimed at the internal body part, and the first and second lighting windows 57 and 59 are exposed from the openings 405 and 406. Thus, the hood 402 does not interfere with application of the excitation light and the white light.

In the above first embodiment, the present invention is applied to the AFI for imaging the autofluorescence emitted from the endogenous fluorescent substance in the living body tissue by application of the excitation light. The present invention is applicable to photodynamic diagnosis (PDD) using a fluorescent labeling agent, or near infrared fluorescence imaging.

In the PDD, the wavelength of fluorescence depends on the type of the fluorescent labeling agent administered to the patient. For example, when Photofrin®, Laserphyrin®, or Visudyne® is administered as the fluorescent labeling agent, fluorescence having a center wavelength of 660 nm is emitted from the living body tissue inside the body cavity upon application of excitation light having a center wavelength of 405 nm. When 5-ALA (5-aminolevulinic acid) is administered as the fluorescent labeling agent, fluorescence having two wavelength peaks at 635 nm and 670 nm is emitted from the living body tissue inside the body cavity upon application of excitation light having a center wavelength of 405 nm. In the near infrared fluorescence imaging, ICG (indocyanine green) is used as the fluorescent labeling agent. When the ICG is administered to the patient, and excitation light having wavelengths around 800 nm is applied to the living body tissue inside the body cavity, near infrared fluorescence having a peak wavelength of 845 nm is emitted therefrom.

The above fluorescent labeling agents used in the PDD and the near infrared fluorescence imaging generally emit the fluorescence having larger intensity than that of the autofluorescence of the AFI. However, there is a case where the fluorescence is short of intensity due to insufficient accumulation of the fluorescent labeling agent in the living body tissue, or the like. In such a case, the frame addition process and the binning process, as described above, are applied to a special image that captures the fluorescence from the labeling agent. The frame addition process and the binning process are modified in accordance with the motion of the object to be inspected, in order to improve the image quality of the special image.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. An electronic endoscope system, comprising:
a light source device for applying illumination light to an internal body part, said illumination light including special light in a specific wavelength band;
an electronic endoscope for capturing an endoscopic image of said internal body part irradiated with said illumination light by using an image sensor, said endoscopic image including a special image captured under said special light;
an object distance detector for detecting from said endoscopic image an object distance including a distance between said image sensor and an inspection area of said internal body part;
a binning processing section for applying a binning process to said special image; and
a binning processing control section for determining a binning number used in said binning process in accordance with said object distance,
wherein said illumination light includes normal light including white light ranging from a blue wavelength band to a red wavelength band,
wherein said endoscopic image includes a normal image of said internal body part irradiated with said normal light, and
wherein said object distance detector obtains said object distance from said normal image.

2. The electronic endoscope system according to claim 1, wherein said special light comprises excitation light for exciting autofluorescence from living body tissue of said internal body part, and
wherein said special image comprises an autofluorescence image that captures autofluorescence emitted from said internal body part irradiated with said excitation light.

3. The electronic endoscope system according to claim 2, wherein said binning processing control section increases said binning number with an increase in said object distance, and decreases said binning number with a decrease in said object distance, in order to adjust an intensity of said autofluorescence image.

4. The electronic endoscope system according to claim 2, wherein said binning processing control section decreases said binning number with an increase in said object distance, and increases said binning number with a decrease in said object distance, in order to adjust a resolution of said autofluorescence image.

5. The electronic endoscope system according to claim 1, wherein said special light comprises narrow band imaging (NBI) light for distinguishing a specific portion including a superficial blood vessel, and
wherein said special image comprises an NBI image of said internal body part irradiated with said NBI light.

6. The electronic endoscope system according to claim 1, wherein said special light comprises narrow band light used for obtaining blood vessel information including a depth of a blood vessel and a blood oxygen saturation, said narrow band light includes two types of light having first and second wavelengths, an absorbance of reduced hemoglobin differs from that of oxygenated hemoglobin at each of said first and second wavelengths, and an amount of difference in said absorbance between said reduced hemoglobin and said oxygenated hemoglobin at said first wavelength differs from that at said second wavelength, and
wherein said special image comprises a blood vessel information image of said internal body part irradiated with said narrow band light.

7. The electronic endoscope system according to claim 1, wherein said binning processing control section increases said binning number with an increase in said object distance between a near view having a short object distance and a far view having a long object distance, and
wherein said binning processing control section sets said binning number larger in a tight close-up state than that in a close-up state, said image sensor is extremely near said inspection area of said internal body part in said tight close-up state, and said image sensor is slightly away from said inspection area in said close-up state as compared to said tight close-up state.

8. The electronic endoscope system according to claim 1, further comprising:
an imaging mode switching section for switching said electronic endoscope system to a special imaging mode, said special imaging mode including:
an AFI (autofluorescence imaging) mode for capturing an autofluorescence image that captures an autofluorescence emitted from living body tissue in a response to excitation light applied from said light source device to said internal body part;
an NBI (narrow band imaging) mode for capturing an NBI image in which a specific portion including a superficial blood vessel is distinguished by applying NBI light from said light source device to said internal body part; and
a blood vessel information obtaining mode for capturing an image of blood vessel information including a depth of a blood vessel and blood oxygen saturation by applying narrow band light from said light source device to said internal body part, said narrow band light including two types of light having first and second wavelengths, an absorbance of reduced hemoglobin differing from that of oxygenated hemoglobin at each of said first and second wavelengths, an amount of difference in said absorbance between said reduced hemoglobin and said oxygenated hemoglobin at said first wavelength differing from that at said second wavelength, and
wherein said binning processing control section determines said binning number in accordance with a type of said special imaging mode and said object distance.

9. The electronic endoscope system according to claim 1, wherein said binning processing section performs a software binning process in which said special image includes plural pixel groups, each of said pixel groups includes plural adjoining pixels, and an intensity of each of said pixel groups corresponds with a sum of an intensity of said pixels contained in said pixel group, and
wherein said binning number includes a number of said pixels contained in each of said pixel groups.

10. The electronic endoscope system according to claim 1, wherein said binning processing section performs a hardware binning process in which said image sensor includes plural pixel groups, each of said pixel groups includes plural adjoining pixels, and said image sensor is controlled so as to output a single imaging signal on a pixel group basis; and
wherein said binning number includes a number of said pixels contained in each of said pixel groups.

11. The electronic endoscope system according to claim 1, wherein said object distance detector detects an exposure amount from said normal image, and calculates said object distance in accordance with said detected exposure amount.

12. The electronic endoscope system according to claim 1, further comprising:
a motion detector for detecting a motion of said inspection area of said internal body part from a plurality of said endoscopic images;
a frame addition section for applying a frame addition process to a plurality of said special images to produce a single high-quality special image; and
a frame addition control section for determining a number of frames to be added in said frame addition process in accordance with said motion of said inspection area detected by said motion detector.

13. A processor device of an electronic endoscope system including a light source device for applying illumination light comprising special light in a specific wavelength band to an internal body part, and an electronic endoscope for capturing an endoscopic image of said internal body part irradiated with said illumination light by using an image sensor, said processor device comprising:
a reception section for receiving said endoscopic image from said electronic endoscope, said endoscopic image including a special image taken under said special light;
an object distance detector for calculating an object distance including a distance between said image sensor and an inspection area of said internal body part based on said endoscopic image;
a binning processing section for applying a binning process to said special image; and
a binning processing control section for determining a binning number used in said binning process in accordance with said object distance,
wherein said illumination light includes normal light including white light ranging from a blue wavelength band to a red wavelength band,
wherein said endoscopic image includes a normal image of said internal body part irradiated with said normal light, and
wherein said object distance detector obtains said object distance from said normal image.

14. An endoscopic image processing method, an endoscopic image comprising an image of an internal body part irradiated with illumination light captured by an image sensor, said illumination light including special light in a specific wavelength band, said endoscopic image including a special image taken under said special light, said endoscopic image processing method comprising:
- detecting an object distance based on said endoscopic image, said object distance including a distance between said image sensor and an inspection area of said internal body part;
- determining a binning number used in a binning process in accordance with said object distance; and
- applying a binning process to said special image with a use of said determined binning number,
- wherein said illumination light includes normal light including white light ranging from a blue wavelength band to a red wavelength band,
- wherein said endoscopic image includes a normal image of said internal body part irradiated with said normal light, and
- wherein, in said detecting, said object distance is obtained from said normal image.

\* \* \* \* \*